US007572436B1

(12) United States Patent
Vernon

(10) Patent No.: US 7,572,436 B1
(45) Date of Patent: Aug. 11, 2009

(54) THIONIN AS AN ANTINEOPLASTIC AND IMMUNOSTIMULANT

(75) Inventor: Leo P. Vernon, Provo, UT (US)

(73) Assignee: Therapro Technologies, Inc., Alpine, UT (US)

( * ) Notice: Subject to any disclaimer, the term of this patent is extended or adjusted under 35 U.S.C. 154(b) by 970 days.

(21) Appl. No.: 10/380,237

(22) PCT Filed: Sep. 11, 2000

(86) PCT No.: PCT/US00/24947

§ 371 (c)(1),
(2), (4) Date: Sep. 10, 2003

(87) PCT Pub. No.: WO02/22159

PCT Pub. Date: Mar. 21, 2002

(51) Int. Cl.
*A61K 38/19* (2006.01)
(52) U.S. Cl. .................... 424/85.2; 424/278.1; 514/2
(58) Field of Classification Search ............ None
See application file for complete search history.

(56) References Cited

U.S. PATENT DOCUMENTS

| | | | |
|---|---|---|---|
| 4,590,071 A | 5/1986 | Scannon et al. | |
| 4,894,227 A * | 1/1990 | Stevens et al. | 424/85.2 |
| 4,894,443 A | 1/1990 | Greenfield et al. | |
| 5,059,413 A | 10/1991 | Reardan et al. | |
| 5,376,640 A | 12/1994 | Miyazaki et al. | |
| 5,518,888 A | 5/1996 | Waldman | |
| 5,536,495 A | 7/1996 | Foster | |
| 5,547,674 A | 8/1996 | Khwaja | |
| 5,565,200 A | 10/1996 | Khwaja | |
| 5,632,983 A | 5/1997 | Hadden | |
| 5,726,156 A | 3/1998 | Girten et al. | |
| 5,767,086 A | 6/1998 | Kauvar et al. | |
| 5,780,037 A | 7/1998 | Khwaja | |
| 5,804,206 A | 9/1998 | D'Amelio et al. | |
| 5,808,140 A | 9/1998 | Haridas | |
| 5,811,452 A | 9/1998 | Ojima et al. | |
| 5,846,548 A | 12/1998 | Bartos | |
| 5,861,483 A | 1/1999 | Wolpe | |
| 5,885,801 A | 3/1999 | Rao | |
| 5,922,902 A | 7/1999 | Haridas | |
| 5,955,432 A | 9/1999 | Kauvar et al. | |
| 6,003,516 A | 12/1999 | Hellstrand et al. | |
| 6,004,558 A | 12/1999 | Thurn et al. | |
| 6,022,535 A | 2/2000 | Bauer et al. | |
| 6,042,848 A | 3/2000 | Lawyer et al. | |

FOREIGN PATENT DOCUMENTS

WO   WO 96/41608   12/1996

OTHER PUBLICATIONS

Berzofsky et al., Journal of Clin. Invest. 2004, vol. 113(11):1515-1525.*
Angerhofer et al., "Phospholipase activation in the cytotoxic mechanism of thionin purified from nuts of *Pyrularia pubera*," *Toxicon.* 28(5):547-557, 1990.
Baxevanis et al., "Mistletoe lectin I-induced effects on human cytotoxic lymphocytes. I. Synergism with IL-2 in the induction of enhanced LAK cytotoxic," *Immunopharm. Immunotoxicol.* 20(3):355-372, 1998.
Bocci, "Mistletoe (viscum album) lectins as cytokine inducers and immunoadjuvant in tumor therapy. A review," *J. Biol. Reg. Homeo. Agents* 7(1):1-6, 1993.
Bohlmann et al., "Wounding and chemicals induce expression of the Arabidopsis thaliana gene Thi2.1, encoding a fungal defense thionin, via the octadecanoid pathway," *FEBS Lett.* 437(3):281-286, Oct. 23, 1998.
Bussing et al., "Accidental cell death and generation of reactive oxygen intermediates in human lymphocytes induced by thionins from Viscum album L.," *Eur. J. Biochem.* 262(1):79-87, May 1999 (abstract only).
Bussing et al., "Expression of mitochondrial Apo2.7 molecules and caspase-3 activation in human lymphocytes treated with the ribosome-inhibiting mistletoe lectins and the cell membrane permeabilizing visotoxins," *Cytometry* 37(2):133-139, Oct. 1, 1999 (abstract only).
Bussing et al., "Generation of reactive oxygen intermediates (ROI) by the thionins from Viscum album L." *Anticancer Res.* 18(6A):4291-4296, Nov.-Dec. 1998.
Büssing et al., "Induction of apoptosis in human lymphocytes treated with *Viscum album* L. is mediated by the mistletoe lectins," *Cancer Lett.* 99:59-72, 1996.
Caaveiro et al., "Interaction of wheat alpha-thionin with large unilamellar vesicles," *Protein Science* 7(12):2567-2577, Dec. 1998.

(Continued)

*Primary Examiner*—Michael Szperka
*Assistant Examiner*—Yunsoo Kim
(74) *Attorney, Agent, or Firm*—Klarquist Sparkman, LLP

(57) ABSTRACT

The invention involves cellular and biological responses to relatively low concentrations of thionin (such as *Pyrularia* thionin), which responses are distinct from the direct cytotoxic effect of high concentrations of thionins on cells. These two separate biological responses of immune cells to thionins are related to the presence of two separate and distinct binding sites on the immune cell, a high affinity binding site that reacts with thionins at low concentrations to stimulate the immune cell to provide antitumor protection, and a low affinity site that is responsible for the direct toxicity of thionins to cells. This invention provides, in certain embodiments, methods for using a thionin, either alone or in combination with an interleukin, for stimulation of the immune system. Particular embodiments provide methods for inhibition of tumor formation and/or tumor metastasis, methods for the stimulation of natural killer cells, methods for the stimulation of T cell lymphocyte differentiation and proliferation, and/or methods for the stimulation of cytokine production by various immune cells. Also provided are compositions that include thionin, e.g., *Pyrularia* thionin, for the treatment and/or prevention of neoplasia, for the treatment of viral infection, for the treatment of immune deficiency (e.g., such as is caused by disease or advancing age). Other embodiments of the invention provide biologically active compounds conjugated or otherwise complexed to the very stable thionin molecule (such as a βME-thionin conjugate), and methods of use of such compounds and/or conjugates for immunostimulation.

19 Claims, 2 Drawing Sheets

OTHER PUBLICATIONS

Figure 2:
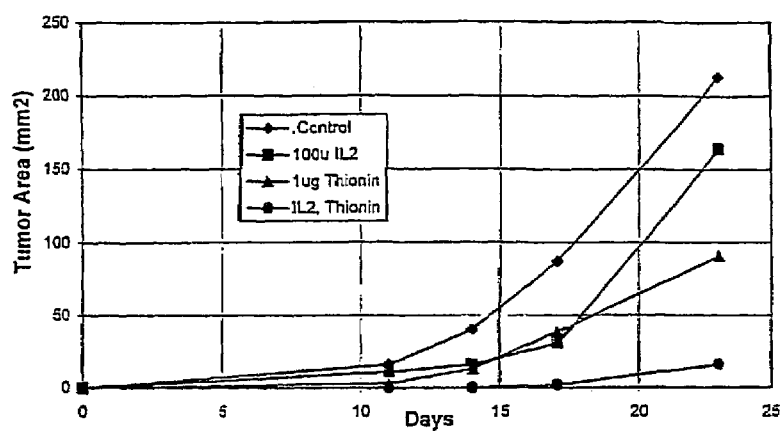

Evans and Vernon, "Cellular membrane responses and phospholipase A$_2$ activation induced by *Pyrularia thionin*," *J. Nat. Toxins* 2(2):143-160, 1993.

Evans et al., "Cellular responses to *Pyrularia thionin* are mediated by Ca$^{2+}$ influx and phospholipase A$_2$ activation and are inhibited by thionin tyrosine iodination." *Proc. Natl. Acad. Sci. USA* 86:5849-5853, Aug. 1989.

Evett et al., "Biological properties of *Pyrularia thionin* prepared from nuts of *Pyrularia pubera*," *Toxicon*. 24(6):622-625, 1986.

Fine et al., "A Specific Stimulator of Granulocyte Colony-Stimulating Factor Accelerates Recovery From Cyclophosphamide-Induced Neutropenia in the Mouse," *Blood* 90(2):795-802, Jul. 15, 1997.

Fracki et al., "Role of tyr and trp in membrane responses of *Pyrularia thionin* determined by optical and nmr spectra following tyr iodination and trp modification," *Toxicon*. 30(11):1427-1440, 1992.

Franz et al., "Differences in toxicity and antigenicity between mistletoe lectin I and viscotoxin A 3," *Biomed. Biochim. Acta* 42(5):K21-K25, 1983.

Froy and Gurevitz, "Membrane potential modulators: a thread of scarlet from plants to humans," *FASEB J.* 12(15):1793-1796, Dec. 1998.

Gasanov et al., "In vitro evaluation of *Pyrularia thionin*—anti-CD5 immunotoxin," *Cancer Immunol. Immunother*. 41:122-128, 1995.

Gasanov et al., " Modification of Phospholipid Membrane Structure by the Plant Toxic Peptide *Pyrularia thionin*," *Arc. Biochem. Biophys*. 301(2):367-374, 1993.

Gasanov et al., "Modulation of Phospholipase A$_2$ Activity by Membrane-active Peptides on Liposomes of Different Phospholipid Composition," *Gen. Physiol. Biophys*. 13:275-286, 1994.

Hamprecht et al., "Mediation of human NK-activity by components in extracts of Viscum album," *Int. J. Immunopharm*. 9(2):199-209, 1987 (abstract only).

Huang et al., "Enhancement of adenylate cyclase activity in S49 lymphoma cell membranes by the toxin thionin from *Pyrularia pubera*," *Toxicon*. 32(7):789-797, 1994.

Huang et al., "Interactions of Thionin from *Pyrularia pubera* with Dipalmitoylphosphatidylglycerol Large Unilamellar Vesicles," *Biochem*. 36(10):2860-2866, 1997.

Judd et al., "*Pyrularia thionin* increases arachidonate liberation and prolactin and growth hormone release from anterior pituitary cells," 30(12):1563-1573, 1992.

Jung et al., "Characterization of cytotoxic proteins from mistletoe (*Viscum album* L.)," *Cancer Lett*. 51:103-108, 1990.

Kolusheva et al., "An investigation of the membranotropic properties of the plant toxin thionin isolated from *Pyrularia pubera*," *Chem. Nat. Comp*. 29(4):523-525, 1993.

Kolusheva et al., "Influence of thionin on the structure of a bilayer and on the intermembrane exchange of lipid material," *Chem. Nat. Comp*. 30(1):68-72, 1994.

Konopa et al., "Isolation of viscotoxins. Cytotoxic basic polypeptides from *Viscum album* L.," *Hoppe Seylers Z. Physiol. Chem*. 361(10):1525-1533, Oct. 1980 (abstract only).

Kushmerick et al., "Functional and structural features of gamma-zeathionins, a new class of sodium channel blockers," *FEBS Lett*. 440(3):302-306, Dec. 4, 1998.

Kuttan et al., "Effect of a preparation from *Viscum album* on tumor development in vitro and in mice," *J. Ethnopharmacol*. 29:35-41, 1990.

Kuttan and Kuttan, "Immunological mechanism of action of the tumor reducing peptide from mistletoe extract (NSC 635089) cellular proliferation," *Cancer Lett*. 66:123-130, 1992.

Kuttan and Kuttan, "Immunomodulatory activity of a peptide isolated from *Viscum album* extract (NSC 635 089)," *Immunolog. Inv*. 21(4):285-296, 1992.

Kuttan et al., "Isolation and identification of a tumour reducing component from mistletoe extract (iscador)," *Cancer Lett*. 41:307-314, 1988.

Osorio e Castro et al., "Action of a thionin isolated from nuts of *Pyrularia pubera* on human erythrocytes," *Toxicon*. 27(5):501-510, 1989.

Osorio e Castro et al., "Hemolysis of erythrocytes and fluorescence polarization changes elicited by peptide toxins, aliphatic alcohols, related glycols and benzylidene derivatives," *Biochim. Biophys. Acta* 1029:252-258, 1990.

Osorio e Castro and Vernon, "Hemolytic activity of thionin from *Pyrularia pubera* nuts and snake venom toxins of *Naja naja* species: *Pyrularia thionin* and snake venom cardiotoxin compete for the same membrane site," *Toxicon*. 27(5):511-517, 1989.

Schaller et al., "Viscotoxin composition of the three European subspecies of *Viscum album*," *Planta Medica* 64(7):677-678, Oct. 1998.

Schrader-Fischer and Apel, "cDNA-derived identification of novel thionin precursors in *Viscum album* that contain highly divergent thionin domains but conserved signal and acidic polypeptide domains," *Plant. Mol. Biol*. (Netherlands) 23(6):1233-1242, Dec. 1993.

Stein et al., "Characterization of granulocyte stimulation by thionins from European mistletoe and from wheat," *Biochim. Biophys. Acta* 1426:80-90, 1999.

Stein and Berg, "Flow cytometric analyses of the specific activation of peripheral blood mononuclear cells from healthy donors after in vitro stimulation with a fermented mistletoe extract and mistletoe lectins," *Eur. J. Cancer* 34(7):1105-1110, Jun. 1998.

Stein et al., "Thionins from *Viscum album* L: influence of the viscotoxins on the activation of granulocytes," *Anticancer Res*. 19(2A):1037-1042, Mar.-Apr. 1999.

Stein et al., "Viscotoxin-free aqueous extracts from European mistletoe (*Viscum album* L.) stimulate activity of human granulocytes," *Anticancer Res*. 19(4B):2925-2928, Jul.-Aug. 1999 (abstract only).

Tan et al., "Enzymatic activities of Calloselasma rhodostoma (Malayan pit viper) venom," *Toxicon*. 24(6):626-630, 1986.

Urech et al., "Comparative study on the cytotoxic effect of visotoxin and mistletoe lectin on tumour cells in culture," *Phytother. Res*. (United Kingdom) 9(1):49-55, 1995 (abstract only).

Vernon et al., "A Toxic Thionin from *Pyrularia pubera*: Purification, Properties, and Amino Acid Sequence," *Arc. Biochem. Biophys*. 238(1):18-29, 1985.

Vernon and Rogers, "Binding properties of *Pyrularia thionin* and *naja naja kaouthia* cardiotoxin to human and animal erythrocytes and to murine P. 388 cells," *Toxicon*. 30(7):711-721, 1992.

Vernon and Rogers, "Effect of calcium and phosphate ions on hemolysis induced by *Pyrularia thionin* and *naja naja kaouthia* cardiotoxin," *Toxicon*. 30(7):701-709, 1992.

Vernon and Bell, "Membrane structure, toxins and phospholipase A$_2$ activity," *Pharmac. Ther*. 54:269-295, 1992.

Vernon, "*Pyrularia thionin*: Physical Properties, Binding to Phospholipid Bilayers and Cellular Responses," in *Natural Toxins II* Singh and Tu (Eds.), Plenum Press, Ch. 22, pp. 279-291, 1996.

Vernon, "*Pyrularia thionin*: Physical Properties, Biological Responses and Comparison to Other Thionins and Cardiotoxin," in *Natural Toxins II* Singh and Tu (Eds.), Plenum Press, pp. 1-26, 1996.

Wang et al., "*Pyrularia thionin* Binding to and the Role of Tryptophan-8 in the Enhancement of Phosphatidylserine Domains in Erythrocyte Membranes," *Biochem*. 32(46):12283-12289, 1993.

Weber et al., "Effects of a standardized mistletoe preparation on metastatic B16 melanoma colonization in marine lungs," *Arzneimittel-Forschung* 48(5):497-502, May 1998.

Wilson et al., "Mechanisms by which thionin induces susceptibility of S49 cell membranes to extracellular phospholipase A$_2$," *Biochim. Biophys. Acta* 1349:142-156, 1997.

Yoon et al., "Inhibitory effect of Korean mistletoe (*Viscum album coloratum*) extract on tumour.angiogenesis and metastasis of haematogenous and non-haematogenous tumour cells in mice," *Cancer Lett*. 97:83-91, 1995.

Yoon et al. "Prophylactic effect of Korean mistletoe (Viscum album coloratum) extract on tumor metastasis is mediated by enhancement of NK cell activity," *Int. J. Immunopharm*. 20(4-5):163-172, 1998.

Zarkovic et al., "Comparison of the effects of *Viscum album* lectin ML-1 and fresh plant extract (Isorel) on the cell growth in vitro and tumorigenicity of melanoma B16F10," *Cancer Biother. Radiopharm*. 13(2):121-131, Apr. 1998 (abstract only).

US 5,637,563, 06/1997, Khwaja (withdrawn)

* cited by examiner

FIGURE 1

|  |  | 1...5 | 1 0 | 1 5 | 2 0 | 2 5 | 3 0 | 3 5 | 4 0 | 4 5 |
|---|---|---|---|---|---|---|---|---|---|---|
| *Pyrularia thionin* | Py | KSCCR | NTWAR | NCYNV | CRLPG | TI SRE | ICAKK | CDCKI | ISGTT | CPSDY P-K |
| *Viscotoxin A3* | A3 | KSCCP | NTTGR | NIYNA | CRLTG | A-PRP | TCAKL | SGCKI | ISGST | CPS-Y PDK |
| *Viscotoxin B* | B | KSCCP | NTT GR | NIYNT | CRLGG | G-SRE | RCASL | SGCK I | ISAST | CPS-Y PDK |
| *Viscotoxin A2* | A2 | KSCCP | NTT GR | NIYNT | CRFGG | G-SRE | VCASL | SGCKI | ISAST | CPS-Y PDK |
| *Phoradendron* | Ph | KSCCP | NTT GR | NIYNT | CRFGG | G-SRP | VCAKL | SGCKI | ISGTK | CDSGW-NH |
| *Crambin* | Cr | TTCCP | SI VA R | SNFNV | CRLPG | T-SEA | ICATY | TGCI I | IPGAT | CPGDY AN- |
|  |  |  |  |  |  | P | L |  |  |  |
| Wheat β | Wb | KSCCK | STLGR | NCYNL | CRARG | A-QK- | LCANV | CRCKL | TSGLS | CPKDF P-K |
| Wheat α 1 | W1 | KSCCR | STLGR | NCYNL | CRARG | A-QK- | LCAGV | CRCKI | SSGLS | CPKGF P-K |
| Wheat α 2 | W2 | KSCCR | TTLGR | NCYNL | CRSRG | A-QK- | LCSTV | CRCKL | TSGLS | CPKGF P-K |
| Barley α | Ba | KSCCR | STLGR | NCYNL | CRVRG | A-QK- | LCAGV | CRCKL | TSTGS | CPKGF P-K |
| Barley β | Bb | KSCCR | STLGR | NCYNL | CRVRG | A-QK- | LCANA | CRCKL | TSGLS CPKGF P-K |

| PT ug/ml | Bnd/Free | SEM |
|---|---|---|
| 0.1 | 0.0177 | 0.0024 |
| 0.2 | 0.0132 | 0.0012 |
| 0.5 | 0.0082 | 0.0010 |
| 1.0 | 0.0056 | 0.0007 |
| 4.5 | 0.0032 | 0.0002 |
| 10 | 0.0026 | 0.0004 |
| 20 | 0.0018 | 0.0001 |

THIONIN AS AN ANTINEOPLASTIC AND IMMUNOSTIMULANT

CROSS REFERENCE TO RELATED APPLICATION

This is the U.S. National Stage of International Application No. PCT/US00/24947, filed Sep. 11, 2000 (which was published in English under PCT Article 21(2)). The entire specification of the international application is incorporated herein by reference.

FIELD

This invention relates to compounds or combinations of compounds that have antineoplastic and/or immunostimulant properties, in particular the combination of IL-2 and a thionin, such as *Pyrularia* thionin.

BACKGROUND

Plants and plant extracts have been used for centuries for medicinal purposes, and bio-prospecting continues in modern times. Identification and characterization of an individual therapeutic property and the responsible compound is a resource-intensive and unpredictable system, but it is vital in the on-going search for therapeutic agents to ameliorate diseases and other detrimental health conditions.

Thionins generally are a class of small and very stable proteins produced by plants, and characterized by containing multiple di-sulfide bridges (usually three or four), being largely basic, and sharing substantial sequence homology. In addition to the European mistletoe viscotoxins, other thionins include phorotoxin, isolated from American mistletoe; purothionins, isolated from wheat; hordothionins, isolated from barley; a venothionin, isolated from rye; and crambin, isolated from cabbage.

Because of their broad distribution among plants, and because of their highly conserved amino acid sequence and structure, thionins may have an important purpose in plants. Thionins isolated from seeds have been speculated to play a role as storage proteins or toxins that protect the seeds from insect, bacterial or fungal invasion. Thionins isolated from leaves also are speculated to serve as toxins. Thionins isolated from barley leaf cells are known to be toxic to certain fungi, and barley plants exposed to spores of such fungi show a rapid increase in transcription levels of the leaf specific thionins.

*Pyrularia* thionin (PT) is a small, strongly basic 47 amino acid peptide produced by the parasitic plant *Pyrularia pubera*. The four disulfide bridges and amino acid sequence of PT place it in the thionin protein family (see FIG. 1). The amino acid sequences of *Pyrularia* thionin, of other thionins, and of related peptides are set forth in FIG. 1. Characterization of the biological properties of *Pyrularia* thionin has been underway for several years, and the toxic properties of this protein have been reported (see, e.g., Vernon et al., *Arch. Biochein. Biophys.* 238:18-29, 1985; Evett et al., *Toxicon* 24:622-625, 1986; and Gasanov et al., *Cancer. Immunol. Immunother.* 41:122-128, 1995).

SUMMARY

The invention described herein is the discovery of a unique and previously unknown immunostimulatory property of thionins, for instance purothionins, hordothionins, venothionin, crambin, phorotoxin, viscotoxins, and *Pyrularia* thionin (PT), at low concentrations. This immunostimulation includes activation of macrophage and natural killer cells, and stimulates the production of interleukin-1 (IL-1) and interleukin-12 (IL-12) by macrophages in splenocyte suspensions. Administration of low doses of thionin also generally stimulates the immune system, leading to an increase in the number of T cells in the spleen and thymus. This reflects a stimulation of T cell development in the thymus, an effect that is different from the activation of mature macrophages and natural killer cells. Thionin-mediated immunostimulation provides protection against tumor formation (e.g., melanoma formation). It can also be used to treat virus infections, or to ameliorate immune deficiency caused, for instance, by disease or advancing age.

The immunostimulations observed with *Pyrularia* thionin, alone or with other immunostimulants, derive from stimulations of cells of the immune system and occur at low concentrations of the thionin. These effects at low thionin concentrations are distinct from the cellular effects observed at higher thionin concentrations, which derive from significant modification of the membrane structure of cells, which modifications affect cell function. These different responses relate to two distinct binding sites for thionin on spleen cells, with the beneficial effects (e.g., immunostimulation and anti-tumor activity) described herein deriving from a high affinity binding site.

The stability of *Pyrularia* thionin in vivo allows it to serve the useful function of delivering beneficial drugs to active sites in the subject when such drugs are conjugated (e.g. chemically conjugated) to the thionin, thus increasing the effectiveness of the drug.

Thus, embodiments of the invention include methods of stimulating immunity, which methods involve administering an immunostimulatory effective amount of an agent to a subject in need thereof, for instance an immunosuppressed subject or a subject who has received an immunosuppressive dose of a chemotherapeutic agent or ionizing radiation. Such administered agent may be a thionin, a thionin-compound conjugate, or an immunostimulatory variant, fragment, mimetic, or analog of such compounds, for example. Representative thionins include, for instance, purothionins, hordothionins, venothionins, crambins, phorotoxins, viscotoxins, and *Pyrularia* thionin. The invention also encompasses methods wherein a therapeutically sufficient amount of a non-thionin immunostimulatory compound (e.g., a cytokine, for instance an interleukin such as IL-2, or a colony stimulating factor) or additional immunostimulant (e.g. GM-CSF, G-CSF, saponin derivative QS-23, or proteins or peptides that are antigenic for target tumor cells) is also administered to the same subject.

In certain disclosed embodiments, the thionin is administered to the subject in a dose that is immunostimulatory but substantially non-cytotoxic, for instance a dose of no more than about 500 µg/Kg body weight, or a dose of between about 50 to about 250 µg/Kg bodyweight.

In certain of the embodiments, stimulating immunity includes inhibiting or preventing tumor (e.g., melanoma or fibrosarcoma) development in the subject (e.g. preventing or slowing tumor development or slowing further development of an existing tumor, or inhibiting metastasis). The methods therefor contemplate administering the immunostimulatory agent to a subject having, or at risk of developing, a tumor, for instance a melanoma or a fibrosarcoma tumor. In certain embodiments, such stimulation of immunity involves activating macrophages, inducing mitosis in an immune cell, stimulating natural killer cell activity (e.g., anti-tumor activity), and/or more generally stimulating the differentiation and proliferation of T cells in the subject.

The invention also provides methods for prolonging the life of and/or effectiveness of a biologically active compound in a subject, by conjugating the compound with thionin to create a compound-thionin complex (conjugate). This conjugate can then be administered to the subject. Such compounds can include chemotherapeutic agents, such as cytotoxic agents (e.g. an alkylating agent or an antimetabolite). More specifically, examples of chemotherapeutic agents include vinblastine, vincristine, vindesine, camptothecin, homoharringtonine, etoposide, teniposide, daunorubicin, doxorubicin, epirubicin, bleomycin, dactinomycin, mitomycin, plicamycin, asparginase, taxol, cisplatin, carboplatin, amsarcrine, dacarbizine (DTIC), hydrea, mitoxantrone, procarbazine, mechlorethamine, chlorambucil, melphalan, cyclophophamide, ifosfamide, busulfan, thiotepa, hexamethylmelamine, methotrexate, purinethol, thioguanine, fludarabine phosphate, pentostatin, cladribine, cytarabine, fluorouracil, floxuridine, Sparfosate (PALA), mechlorethanime, melphalan, uracil mustard, carmustine (BCNU), lomustine (CCNU), semustine (methyl-CCNU), streptozocin, cytarabine, mercaptopurine, thioguanine, hydroxyurea, mitotane (o,p'-DDD), aminoglutethimide, prednisone, progestins, estrogens, tamoxifen, androgens, and biologically active analogs, derivatives, mimetics or fragments thereof, as well as pharmaceutically acceptable salts thereof. In certain of these embodiments, the thionin-conjugate complex may be targeted to certain cells in the subject.

The invention also encompasses such compound-thionin conjugates/complexes.

Further embodiments are methods of increasing an immunostimulating property of a single or a mixture of non-thionin immunostimulants, which method includes co-administering with the non-thionin immunostimulant(s) an effective amount of a thionin (e.g. *Pyrularia* thionin), or a biologically active derivative, mimetic, fragment or analog thereof. Such non-thionin immunostimulants include, but are not limited to, GM-CSF, G-CSF, saponin derivative QS-23, and proteins or peptides that are antigenic for target tumor cells. In specific embodiments, the method further includes co-administering an antigenic peptide or protein, such as keyhole limpet hemocyanin, or an antigenic fragment or variant thereof, with the non-thionin immunostimulant and thionin.

Also encompassed by the invention are therapeutic compositions that comprise an immunostimulatory effective amount of a thionin and an immunostimulatory effective amount of IL-2.

A further embodiment of the invention is a method of stimulating immunity in a subject, which method includes administering to the subject an immunostimulatory therapeutically effective amount of PT. Such amount can in some instances be an amount less than a dose that is directly cytotoxic to cells.

The foregoing and other features and advantages of the invention will become more apparent from the following detailed description of several embodiments, which proceeds with reference to the accompanying figures.

BRIEF DESCRIPTION OF THE FIGURES

FIG. 1 is an alignment showing the amino acid sequences of *Pyrularia* thionin and several viscotoxins, other thionins, and related peptides.

FIG. 2 is a graph showing the inhibitory effect of thionin and thionin/IL-2 on tumor formation. Results from a typical experiment are shown, with tumor area plotted on one axis and the time in days after injection of B16 melanoma cells plotted on the other axis.

FIG. 3 is a graph that represents the intensity of binding of PT to murine Balb/C splenocytes. The PT was labeled with radioactive iodine ($^{125}I$), the extent of binding at different concentrations of labeled PT was determined, and the molecules of thionin bound per cell calculated.

DETAILED DESCRIPTION

I. Abbreviations and Definitions

Abbreviations

βME: β-mercaptoethanol
IL-[ ]: Interleukin-[ ], i.e., IL-2 represents interleukin-2
KLH: keyhole limpet hemocyanin
G-CSF: granulocyte colony-stimulating-factor
GM-CSF: granulocyte-macrophage colony-stimulating-factor
NK: natural killer cells
PBL: peripheral blood lymphocyte
PT: *Pyrularia* thionin

Definitions

The following definitions and methods are provided to better define the present invention and to guide those of ordinary skill in the art in the practice of the present invention. Definitions of common terms in molecular biology may also be found in Rieger et al., *Glossary of Genetics: Classical and Molecular,* 5th edition, Springer-Verlag: New York, 1991; and Lewin, Genes VII, Oxford University Press: New York, 1999. The terms "a" and "the" are understood to include the plural of the object referred to, as well as the singular, unless the context indicates otherwise.

Analog: A molecule that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in *Remington: The Science and Practice of Pharmacology,* 19$^{th}$ Edition (1995), chapter 28. A derivative is a biologically active molecule derived from the base structure. A mimetic is a biomolecule that mimics the activity of another biologically active molecule. Biologically active molecules can include both chemical structures and peptides of protein entities that mimic the biological activities of the thioinin molecules of the present invention.

Animal: Living multi-cellular vertebrate organisms, a category that includes, for example, mammals and birds. The term mammal includes both human and non-human mammals. Similarly, the term "subject" includes both human and veterinary subjects.

Cancer: A cancer is a biological condition in which a malignant tumor or neoplasm has undergone characteristic anaplasia with loss of differentiation, increased rate of growth, invasion of surrounding tissue, and which is capable of metastasis.

By way of example, and without limitation thereto, the term cancer includes breast carcinomas (e.g., lobular and duct carcinomas), and other solid tumors, sarcomas, and carcinomas of the lung like small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, bladder carcinoma including transitional cell carcinoma, adenocarcinoma, and squamous carcinoma, renal cell adenocarcinoma, endometrial carcinomas including adenocarcinomas and mixed Mullerian tumors (carcinosarcomas), carcinomas of the endocervix, ectocervix, and vagina such as adenocarcinoma and squamous carcinoma, tumors of the skin like squamous cell carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcomas of bone and cartilage.

Chemotherapeutic agents, which can be used to treat neoplastic growths (including tumors) include, but are not limited to, vinblastine, vincristine, vindesine, camptothecin, homoharringtonine, etoposide, teniposide, daunorubicin, doxorubicin, epirubicin, bleomycin, dactinomycin, mitomycin, plicamycin, asparginase, taxol, cisplatin, carboplatin, amsarcrine, dacarbizine (DTIC), hydrea, mitoxantrone, procarbazine, mechlorethamine, chlorambucil, melphalan, cyclophosphamide, ifosfamide, busulfan, thiotepa, hexamethylmelamine, methotrexate, purinethol, thioguanine, fludarabine phosphate, pentostatin, cladribine, cytarabine, fluorouracil, floxuridine, Sparfosate (PALA), mechlorethanime, melphalan, uracil mustard, carmustine (BCNU), lomustine (CCNU), semustine (methyl-CCNU), streptozocin, cytarabine, mercaptopurine, thioguanine, hydroxyurea, mitotane (o,p'-DDD), aminoglutethimide, prednisone, progestins, estrogens, tamoxifen, androgens, and biologically active analogs, derivatives, mimetics or fragments thereof.

Co-administration: This term refers to administering two or more compounds (e.g., therapeutic compounds) to the same subject (or cell or system) as part of the same treatment. Compounds that are co-administered can be applied as a mixture, at the same time but separately, or sequentially within a time-frame such that they exhibit activity(ies) on the system that overlap.

Differentiation: Process by which cells become more specialized to perform biological functions, and differentiation is a property that is totally or partially lost by cells that have undergone malignant transformation.

Immunostimulatory compound: A compound that exerts a stimulatory effect on at least one immune cell or class of immune cells. Endogenous immunostimulatory compounds include immunostimulatory cytokines, such as IL-1, IL-2, IL-3, IL-4, IL-5, IL-6, IL-7, IL-9, IL-11, IL-13, IL-14, IL-15, G-CSF, GM-CSF, erythropoietin, thrombopoietin, stem cell factor, and flk2/flt3 ligand.

Incorporation of [a compound] into pharmaceutical compositions: Pharmaceutical compositions that include at least one active ingredient may be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like.

Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, for instance another immunostimulant, also may be included.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g. syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those having ordinary skill in the art.

Injectable composition: A pharmaceutically acceptable fluid composition comprising at least one active ingredient, but that may contain two or more active ingredients in combination. The active ingredient(s) are usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are beneficial for use with this invention are conventional; appropriate formulations are well known in the art.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linker: A peptide, usually but not necessarily between two and 150 amino acid residues in length, that serves to join two protein domains in a multi-domain fusion protein. Examples of specific linkers can be found, for instance, in Hennecke et al. (*Protein Eng.* 11(5):405-10; 1998); and U.S. Pat. Nos. 5,767,260 and 5,856,456.

Depending on the domains being joined, and their eventual function in the fusion protein, linkers may be from about two to about 150 amino acids in length, though these limits are given as general guidance only. The tendency of fusion proteins to form specific and non-specific multimeric aggregations is influenced by linker length (Alfthan et al., *Protein Eng.* 8(7):725-731, 1998). Thus, shorter linkers will tend to promote multimerization, while longer linkers tend to favor maintenance of monomeric fusion proteins. Aggregation can also be minimized through the use of specific linker sequences, as demonstrated in U.S. Pat. No. 5,856,456.

Linkers may be repetitive or non-repetitive. One classical repetitive linker used in the production of single chain Fvs (SCFvs) is the (Gly4Ser)$_3$ (or (GGGGS)$_3$ or (G$_4$S)$_3$) linker. More recently, non-repetitive linkers have been produced, and methods for the random generation of such linkers are known (Hennecke et al., *Protein Eng.* 11:405-410, 1998). In addition, linkers may be chosen to have more or less secondary character (e.g., helical character, U.S. Pat. No. 5,637,481) depending on the conformation desired in the final fusion protein. The more secondary character a linker possesses, the more constrained the structure of the final fusion protein will be. Therefore, substantially flexible linkers that are substantially lacking in secondary structure allow flexion of the fusion protein at the linker.

Linking group: The "chemical arm" between a protein, peptide, or polypeptide and a compound (such as a drug or drug derivative). To accomplish the requisite chemical structure, each of the reactants must contain the necessary reactive groups. Representative combinations of such groups are amino with carboxyl to form amide linkages; carboxy with hydroxy to form ester linkages or amino with alkyl halides to form alkylamino linkages; thiols with thiols to form disulfides; or thiols with maleimides or alkylhalides to form thioethers. Hydroxyl, carboxyl, amino and other functionalities, where not present may be introduced by known methods.

A wide variety of linking groups may be employed. The structure of the linkage should be a stable covalent linkage formed to conjugate the compound of interest to the protein, polypeptide or peptide. The covalent linkages should be stable relative to the solution conditions under which the ligand and linking group are subjected, such as physiological conditions. Generally preferred linking groups will be from 1 to about 20 carbons and up to about 10 hetero-atoms (NH, O, S) and may be branched or straight chain. Without limiting the foregoing, combinations of atoms that are chemically compatible will be included in the linking group. Chemically compatible linking groups include, for example, amide, ester, thioether, thiol ester, keto, hydroxyl, carboxyl, ether groups in combinations with carbon-carbon bonds.

Mimetic: A biological compound (such as a peptide) that mimics the effect of a pharmaceutical, for example a peptide that mimics the effect of a thionin by binding to a high-affinity thionin-binding site on an immune cell.

Neoplasm: A new and abnormal growth, particularly a new growth of tissue or cells in which the growth is uncontrolled and progressive. A tumor is an example of a neoplasm.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Operably linked nucleic acid: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Modifications: The present invention includes biologically active molecules that mimic the specific biological action of the active proteins described herein. The invention includes use of synthetic embodiments of naturally-occurring proteins described herein, as well as analogues (non-peptide organic molecules), derivatives (chemically functionalized protein molecules obtained starting with the disclosed peptide sequences) and variants (homologs) of these proteins that have the indicated biological activity. Each protein (or peptide) of the invention is comprised of a sequence of amino acids, which may be either L- and/or D-amino acids, naturally occurring and otherwise.

Pharmaceutically acceptable carriers: The pharmaceutically acceptable carriers useful in this invention include at least conventional pharmaceutically acceptable carriers *Remington's Pharmaceutical Sciences*, by E. W. Martin, Mack Publishing Co., Easton, Pa., 15th Edition (1975), describes compositions and formulations suitable for pharmaceutical delivery of the immunostimulants herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent or drug: A chemical compound or composition capable of inducing a desired therapeutic or prophylactic effect when properly administered to a subject.

Protein Purification: The polypeptides of the present invention can be purified by, for instance, methods of physical purification from raw materials (such as raw plant materials) known to those of ordinary skill in the art, as well as recombinant expression and subsequence purification. See, e.g., *Guide to Protein Purification*, ed. Deutscher, *Meth Enzymol.* 185, Academic Press, San Diego, 1990; and Scopes, *Protein Purification: Principles and Practice*, Springer Verlag, New York, 1982.

Purified, Homogeneous Compounds: The term purified does not require absolute purity; rather, it is intended as a relative term. Thus, for example, a purified protein preparation is one in which the specified protein is more enriched than the protein is in its natural environment within a cell or other production system. A polypeptide is "purified" if it has been substantially separated from contaminants, e.g., cellular components (nucleic acids, lipids, carbohydrates, and other polypeptides) that naturally accompany it. Such a polypeptide can also be referred to as "pure" or "homogeneous" or "substantially" pure or homogeneous. Purified is intended to be a relative term, and a polypeptide (or other specified molecule) is purified when at least 50-90% by weight of a sample is composed of the polypeptide. In certain highly purified preparations, the subject polypeptide will be at least 95% or more of the sample, even as much as 99% or more. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Recombinant Nucleic Acid: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Recombinant Protein: A recombinant protein is one encoded by a recombinant nucleic acid molecule.

Specific binding agent: An agent that binds substantially only to a defined target. As used herein, the term "thionin specific binding agent" includes anti-thionin antibodies and other agents that bind substantially only to a thionin protein, such as *Pyrularia* thionin. The antibodies may be monoclonal or polyclonal antibodies that are specific for a thionin, as well as immunologically effective (e.g., specifically binding) portions ("fragments") thereof. Preferably, the antibodies used in the present invention are monoclonal antibodies (or immunologically effective portions thereof) and may also be humanized monoclonal antibodies (or immunologically effective portions thereof). Anti-thionin peptide antibodies may also be produced using standard procedures described in a number of texts, including *Antibodies, A Laboratory Manual*, by Harlow and Lane, Cold Spring Harbor Laboratory (1988). Thionin, however, appears to be poorly immunogenic and as such it may be advantageous to genetically engineer an epitope tag into the molecule if it is desirable to trace it using an antibody or functional antibody fragment. Epitope tags (such as c-myc, HA (hemagglutinin), and FLAG), and the procedures for engineering such into proteins, are well known to one of ordinary skill in the art.

The determination that a particular agent binds substantially only to a thionin (or a tagged thionin) may readily be made by using or adapting routine procedures. One suitable in vitro assay makes use of the Western blotting procedure (described in many standard texts, including *Antibodies, A Laboratory Manual* by Harlow and Lane). Western blotting may be used to determine that a given binding agent, such as a monoclonal antibody, binds substantially only to thionin (or tagged thionin).

Shorter fragments of antibodies can also serve as specific binding agents. For instance, FAbs, Fvs, and single-chain Fvs (SCFvs) that bind to thionin would be thionin-specific binding agents. These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two Fab' fragments are obtained per antibody molecule; (3) (FAb')2, the fragment of the antibody obtained by treating whole antibody with the enzyme pepsin without subsequent reduction; (4) F(Ab')2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine (for instance, see Better and Horowitz, *Methods. Enzymol.*, 178:476-496, 1989).

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl Acad. Sci. USA* 85: 2444, 1988; Higgins & Sharp *Gene,* 73: 237-244, 1988; Higgins & Sharp *CABIOS* 5: 151-153, 1989; Corpet et al, *Nuc. Acids Res.* 16, 10881-90, 1988; Huang et al., *Computer Appls. in the Biosciences* 8, 155-65, 1992; and Pearson et al, *Meth. Mot Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a thionin encoding sequence (e.g., a *Pyrularia* thionin encoding sequence) will typically hybridize to a probe based on either an entire thionin encoding sequence, or selected portions of the encoding sequence, under wash conditions of 2×SSC at 50° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Therapeutic agent: As used herein, this term includes treating agents, prophylactic agents, and replacement agents.

Therapeutically effective amount of (a substance): A quantity of an active compound (or mixture of active compounds) sufficient to achieve a desired effect in a subject being treated, such as an immunostimulatory effect.

The immunostimulatory uses of the proteins (and protein combinations) disclosed in the present invention have equal application in medical and veterinary settings. Therefore, the general terms "subject" and "subject being treated" are understood to include all animals, including by way of example humans or other simians, dogs, cats, horses, and cows, since all animals have an immune system and therefore may benefit from treatment with an immunostimulant.

Thionin: Thionins generally are a class of small toxin proteins produced by plants, and characterized by containing multiple di-sulfide bridges (usually three or four), being largely basic, and sharing substantial sequence homology.

The thionins include the purothionins, isolated from wheat: hordothionins, isolated from barley; a venothionin, isolated from rye; and crambin, isolated from cabbage. The amino acid sequences of *Pyrularia* thionin, of other thionins, and of related peptides are set forth in FIG. 1.

*Pyrularia* thionin (PT) is a specific example of a thionin; PT is isolated from *Pyrularia* species, particularly *P. pubera*, a parasitic plant of the order *Santalales*.

Tumor: A neoplasm that may be either malignant or non-malignant and includes both solid and non-solid tumors (such as hematologic malignancies). "Tumors of the same tissue type" refers to primary tumors originating in a particular organ (such as breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular.

Variant thionins and thionin-related peptides: Thionin-related peptides having one or more amino acid substitutions, one or more amino acid deletions, and/or one or more amino acid insertions, so long as the molecule retains the property of stimulating the immune system when applied at a low level, for instance at about 0.003 to about 0.1 µg/ml in in vitro test systems or about 3 µg applied to a 20 g mouse. Specific immunostimulatory effects of thionins, that would also be found in a biologically active variant thionin or biologically active thionin-related peptide, are described herein. Conservative amino acid substitutions may be made in at least one position, for example 2, 3, 4, 5 or even 10 positions, as long as the peptide retains immunostimulatory activity, as readily measured by, for instance, using a mitogen assay, natural killer assay, or by tumor or metastasis inhibition assays, as disclosed herein.

Unless otherwise defined, all technical and scientific terms used herein are defined as those known to a person having ordinary skill in the art to which this invention belongs would understand them to be. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

II. Thionin

A. Bioactivities

The invention described herein is the discovery of a unique and previously unknown immunostimulatory property of thionin, for instance *Pyrularia* thionin (PT), at low concentrations. This immuno-stimulation includes activation of macrophage and natural killer cells, and stimulates the production of interleukin-1 (IL-1) and interleukin-12 (IL-12) by macrophages in splenocyte suspensions. Administration of somewhat higher doses of thionin also more generally stimulates the immune system, leading to an increase in the number of T cells in the spleen and thymus. This reflects a stimulation of T cell development in the thymus, an effect that is different from the activation of mature macrophages and natural killer cells. Thionin-mediated immuno-stimulation provides protection against tumor formation (e.g., melanoma formation). It can also be used to treat virus infections, or to ameliorate immune deficiency caused, for instance, by disease or advancing age.

These immunostimulatory effects are felt at surprisingly low concentrations of thionin (e.g., in the range of about 0.003 to about 0.1 µg/ml). Cells exhibit distinct and different responses to application of thionin (e.g., *Pyrularia* thionin) at low versus high concentrations. This reflects the discovery that there are two thionin-binding elements on immune cells. The activity reported herein relates to a high affinity site (with a dissociation constant of 0.065 µM), which mediates stimulation of immune cells to provide antitumor protection at low thionin concentrations. The low affinity binding site is involved in the binding of PT to phosphatidylserine (PS) or other basic phospholipids in the membrane, leading to membrane disruption and then to cell death at high PT concentrations (direct toxicity).

An example of an immunostimulatory effect of PT administration to mice is an observed increase in the number of T cells in the spleen and thymus. This effect takes place when 10 µg of PT are injected intraperitoneally into Swiss Webster mice. This reflects a stimulation of T cell development in the thymus, an effect that is different from the activation of mature macrophages and natural killer cells.

Thionin immunostimulatory activity is enhanced when it is applied in conjunction with an interleukin, such as interleukin-2 (IL-2). Combination treatment using IL-2 and PT prevents or reduces tumor development and slows growth of established tumors. These results are consistent with activation of natural killer cells. This treatment also inhibits metastasis (e.g. of melanoma tumors), and protects against other cancers including fibrosarcoma.

In in vitro experiments, murine spleen cells exhibit consistent responses (stimulation of mitogen activity, and natural killer cell activity) to application of the thionin PT. In addition, injection of PT provides protection against tumor formation and metastasis. Co-administration of thionin with other immunostimulatory compounds, for instance IL-2 or granulocyte-macrophage colony-stimulating factor (GM-CSF), synergistically enhances the observed specific and general immunostimulatory responses.

Without meaning to be bound to any single mechanism, thionin antitumor activity appears to be mediated (at least in part) through activation of NK cells. The major indication of the involvement of NK cells may be the synergistic stimulation observed when the immunostimulant IL-2 is co-administered. Also, anti-tumor activity of thionin is increased in the presence of indomethacin, an inhibitor of prostaglandin A2 formation. Prostaglandin A2 is known to inhibit NK activity.

These in vitro immunostimulatory effects are observed at relatively low concentrations of thionin (e.g., in the range of about 0.003 to about 0.1 µg/ml of *Pyrularia* thionin), much lower than levels (2 to 30 µg/ml) previously described as necessary to stimulate cytotoxic cellular responses to PT. The distinct and different responses of cells to PT at low and high concentrations reflect the surprising discovery that there are two PT-responsive binding elements on immune cells. The immunostimulatory activities reported herein relate to a high affinity site (with a dissociation constant of about 0.065 µM).

In contrast, the low affinity site (with a dissociation constant of about 1.6 µM) is responsible for cytotoxic effects caused by PT when it is applied to cells at a high concentration. High concentrations of PT bind to phosphatidylserine or other phospholipids in the phospholipid bilayer of cells, which leads to perturbation of the cell membrane, opening of a calcium channel, activation of endogenous phospholipase A2, membrane blebbing, and eventual cell death.

B. Sequence Variants

The lipid binding characteristics and immunostimulatory activity of the thionin proteins lie not totally in the precise amino acid sequence, but at least partially in the three-dimensional structure and resulting surface properties of the protein inherent in the amino acid sequences encoded by the DNA sequences. It is possible to recreate the physical characteristics of any of these peptides, proteins or protein domains of this invention by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a functional binding peptide.

Variant thionin related peptides include those that differ in amino acid sequence from the disclosed sequences (see FIG. 1), but that share structurally significant sequence homology with any of the provided proteins. Certain of such variants are characterized by having thionin-like biological activity, such as high-affinity immunostimulatory activity as described herein.

TABLE 1

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein structure may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g. seryl or threonyl) is substituted for (or by) a hydrophobic residue (e.g. leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g. phenylalanine) is substituted for (or by) one lacking a side chain (e.g., glycine). Even though some of these more significant changes are made, the resultant variants may fall within the scope of the claims. Such more significant variants can, as with conservative variants, be assayed for thionin-like bioactivity using, for instance, the assays described herein.

Amino acid positions 9-14 of the thionin compounds are the most highly conserved (FIG. 1). This may indicate that this region is particularly responsible for their biological activities. Therefor, in thionin variants in which it is essential to maintain thionin function (e.g., immunostimulatory activity), substitutions are ideally avoided at amino acid positions 9-14 where it is important to retain bioactivity of the resultant thionin variant. Likewise, in certain thionin variants in which it is essential to maintain stability and/or secondary structure, substitutions are avoided at the cysteine residues that form the disulfide bridges within the thionin.

Variant binding peptides or peptide-encoding sequences may be produced by standard DNA mutagenesis techniques, for example, M13 primer mutagenesis. Details of these techniques are provided in Sambrook (In *Molecular Cloning: A Laboratory Manual*, Cold Spring Harbor, N.Y., 1989), Ch. 15. By the use of such techniques, variants may be created which differ in minor ways from the polo-box peptide-encoding sequences disclosed. Peptide sequences which are derivatives of those specifically disclosed herein and that differ from those disclosed by the deletion, addition, or substitution of amino acids while still encoding a peptide or protein that competes with a native thionin for binding to a specific site (of either high or low affinity), thereby modulating a thionin-mediated activity (e.g., an immunostimulatory activity, particularly an activity that occurs at a low thionin concentration as described herein) in a cell or cell-free system, are comprehended by this invention.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed fusion sequences. Based upon the degeneracy of the genetic code, variant DNA molecules may be derived from encoding sequences disclosed herein using standard DNA mutagenesis techniques as described above, or by synthesis of DNA sequences. Thus, this invention also encompasses nucleic acid sequences which encode a polo-box related peptide, but which vary from the disclosed sequences by virtue of the degeneracy of the genetic code.

C. Peptide Modifications

The present invention includes biologically active molecules that mimic the action of the thionins and thionin-conjugates of the present invention, and specifically compete with a thionin for binding at a specific cellular site (such as a high affinity site as defined herein). The proteins and peptides of the invention include synthetic embodiments of naturally-occurring proteins described herein, as well as analogues (non-peptide organic molecules), derivatives (chemically functionalized protein molecules obtained starting with the disclosed peptide sequences) and variants (homologs) of these proteins that specifically compete with native polo-like kinase for binding, e.g., binding to an element of the neck filaments or other cytokinetic structure. Each protein or peptide of the invention is comprised of a sequence of amino acids, which may be either L- and/or D-amino acids, naturally occurring and otherwise.

Proteins and peptides may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1,R_2$ wherein $R_1$ and $R_2$ are each independently H or $C_1$-$C_{16}$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the protein side chains may be converted to $C_1$-$C_{16}$ alkoxy or to a $C_1$-$C_{16}$ ester using well-recognized techniques. Phenyl and phenolic rings of the protein side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the protein side chains can be extended to homologous $C_2$-$C_4$ alkylenes. Thiols can be protected with any one of a number of well-recognized protecting groups, such as acetamide groups. Those having ordinary skill in the art will also recognize methods for introducing cyclic structures into the proteins of this invention to select and provide conformational constraints to the structure that result in enhanced stability.

Peptidomimetic and organomimetic embodiments are also within the scope of the present invention, whereby the three-dimensional arrangement of the chemical constituents of such peptido- and organomimetics mimic the three-dimensional arrangement of the protein backbone and component amino acid side chains in the bispecific neutralizing fusion protein, resulting in such peptido- and organomimetics of the proteins of this invention having measurable or enhanced neutralizing ability. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the invention are mimetics prepared using such techniques that produce neutralizing fusion proteins.

D. Assaying Thionins or Thionin-Derivatives

The chemical, physical and biological activity (particularly, the immunostimulatory activities) of the disclosed thionins can be readily assessed using the assays disclosed herein, for example the assays of Examples 1-4. Among other uses, functional assays of protein function permit optimization of the dosage amounts of each protein effective in therapeutic uses, the design (including length) of thionin-derived molecules, for instance those containing conservative or non-conservative amino acid substitutions, and the comparison of other thionin with the *Pyrularia* thionin activities described herein as examples. These assays can also be used to test known thionin proteins, as well as newly identified thionins or putative thionins, or thionin variants and mimetics, for immunostimulatory bioactivity. Candidate agents can initially be screened, for example in the mitogen assay, for subsequent selection and testing in one or more of the assays of Examples 2-4.

Thionin immunostimulatory activity is the ability of a protein to stimulate an immune response in an immune cell, an immune system, and/or more generally in an animal. More specifically, low-dosage thionin-related immunostimulation includes those effects that can be seen when thionin is applied to an in vitro system using a dosage of less than 2 µg/ml, and more particularly when less than 1 µg/ml (e.g., about 0.1 µg/ml to as little as 0.003 µg/ml or less). In an in vivo system, these effects are seen at an application level of about 1 µg to about 5 µg in a 20 g mouse, or about 50 to about 250 µg/Kg body weight. Specific immunostimulatory effects that may be involved include stimulation of T-cell production, stimulation of interleukin production (e.g., production of IL-1 and/or IL-12 by macrophages), and activation of natural killer cells and/or macrophages. Many of these immunostimulatory effects can be synergistically enhanced by the co-administration of one or more additional immunostimulants, including for instance immunostimulatory interleukins (such as IL-2) and colony stimulating factors (such as GM-CSF).

Methods for examining thionin-mediated immunostimulation include those disclosed herein, such as direct measurement of the activation or proliferation of one or more immune cell types, or increased interleukin production (e.g., IL-1 or IL-12). Secondary effects of immune stimulation can also be measured as described herein, for instance by examining the formation of tumors, the relative rate of growth of a tumor, or tumor metastasis, or by resistance of an organism treated with the test compound to viral or other infection. Control molecules may be included in each assay. Control molecules may include, for instance, thionin-related peptides in which the amino acids responsible for formation of one or more disulfide bridges, responsible for post-translational modification of the thionin molecule (e.g., glycosylation or phosphorylation), or otherwise necessary for one of the functions discussed herein have been replaced. In the case of thionin-conjugates, control molecules may include any portion of the conjugate system (e.g., in the example presented below, describing a thionin-βME conjugate, such controls would include thionin and βME).

III. Thionin as a Stabilizing Carrier Protein

Because of its unique structure, *Pyrularia* thionin is a very compact and extremely stable molecule, whose interaction with cell membranes is not influenced by exposing it to a temperature of 70° C. This extreme stability is due to the four disulfide bonds which form between the eight cysteine residues in the protein. This tight structure also makes the protein resistant to the common proteases found in blood. Importantly, because of its tight structure and resistance to the action of the common proteases, PT is not immunogenic. Taken together, these properties of extreme stability and lack of immunogenicity make PT an excellent vehicle for delivery of drugs to their site of action in the body.

PT, and more generally thionins, are therefore excellent vehicles for delivery of drugs or other therapeutic compounds to cells of a subject. This function is a result of the extreme stability of thionins, due at least in part to the multiple disulfide bridges that constrain the three-dimensional form of the protein. By way of example, PT can be attached to a compound of interest (e.g., through chemical conjugation or, where the compound is a protein, genetic fusion with an encoding sequence), and the conjugate delivered to the subject. This system increases the stability of the passenger compound (e.g., βME, a known stimulator of immune responses of lymphocytes), and facilitates its delivery to cells.

The use of a thionin as a stabilizing carrier protein is demonstrated by conjugation of PT to β-mercaptoethanol (βME), a known stimulator of immune responses of lymphocytes (see below). The PT-βME conjugate shows significantly greater activity when compared to PT alone. The ease of affecting such conjugations to the strongly basic PT makes it an ideal candidate for the delivery of other drugs and stimulants in vivo.

Other possible passenger compounds include, by way of example only: chemotherapeutic agents (such as adriamycin, methotrexate, or other agents that bind to and affect the cell membrane), and peptides that are antigenic for tumor cells.

Methods of attaching a passenger compound to a thionin include chemical linking (such as specific cross-linking, as described herein) and genetic (recombinant) fusion. Methods for the production of fusion proteins are replete in the art, and can be found for instance in U.S. Pat. Nos. 6,022,535 and 6,066,318, herein incorporated by reference:

IV. Expression and Purification of Thionins or Related Proteins

A. Expression of Thionin or Derivatives or Fusions Thereof.

One skilled in the art will understand that there are myriad ways to express a recombinant protein (e.g., a thionin, thionin variant, or thionin recombinant fusion as described herein) such that it can subsequently be purified. In general, an expression vector carrying the nucleic acid sequence that encodes the desired protein will be transformed into a microorganism for expression. Such microorganisms can be prokaryotic (bacteria) or eukaryotic (e.g., yeast). One example species of bacteria that can be used is *Escherichia coli* (*E. coli*), which has been used extensively as a laboratory experimental expression system. An eukaryotic expression system can be used where the protein of interest requires eukaryote-specific post-translational modifications such as glycosylation, phosphorylation, or complex secondary or tertiary structure (which may be modulated by the activity of one or more chaperones or other accessory proteins). Also, protein can be expressed using a viral (e.g., vaccinia) based expression system.

Protein can also be expressed in animal cell tissue culture, and such a system can be used where animal-specific protein modifications are desirable or required in the recombinant protein. Likewise, plant tissue culture can be used, and is recommended where there are plant-specific protein modifications (e.g., post-translational modifications) of the protein that are desirable or required.

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter can be used. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits are produced commercially. See, for instance, the QIAexpress™ expression system from QIAGEN (Chatsworth, Calif.) and various expression systems provided by INVITROGEN (Carlsbad, Calif.). Depending on the details provided by the manufactures, such kits can be used for production and purification of the disclosed thionins, thionin-related peptides and proteins, and thionin fusions.

B. Purification.

One having ordinary skill in the art will understand that there are myriad ways to purify recombinant polypeptides, and such typical methods of protein purification may be used to purify the disclosed therapeutic thionins and related proteins. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused to the protein and used to facilitate polypeptide purification. A specific proteolytic site, for instance a thrombin-specific digestion site, can be engineered into the protein between the tag and the fusion itself to facilitate removal of the tag after purification.

Commercially produced protein expression/purification kits provide tailored protocols for the purification of proteins made using each system. See, for instance, the QIAexpress™ expression system from QIAGEN (Chatsworth, Calif.) and various expression systems provided by INVITROGEN (Carlsbad, Calif.). Where a commercial kit is employed to produce a bispecific fusion protein, the manufacturer's purification protocol is a particularly disclosed protocol for purification of that protein. For instance, proteins expressed with an amino-terminal hexa-his tag can be purified by binding to nickel-nitrilotriacetic acid (Ni-NTA) metal affinity chromatography matrix (*The QIAexpressionist*, QIAGEN, 1997).

If the thionin or thionin-related peptide is produced in a secreted form, e.g., secreted into the milk of a transgenic animal, purification will be from the secreted fluid. Alternately, purification may be unnecessary if the protein can be applied directly to the subject in the secreted fluid (e.g., milk).

V. Incorporation into Pharmaceutical Compositions

Pharmaceutical compositions that include at least one thionin protein as described herein as an active ingredient, or that include both a thionin and an interleukin (e.g. IL-2) as active ingredients, may be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, for instance another immunostimulant, also may be included. Immunostimulants include COX-2 inhibitors, IL-12, saponins (e.g. QS-23), and N-acetyl-cysteine, for example.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise a thionin, or a thionin and an interleukin (e.g., IL-2), in some embodiments of the invention will be formulated in unit dosage form, suitable for individual administration of precise dosages. One possible unit dosage contains approximately 1.5 mg of thionin, with or without approximately 50,000 units of IL-2 (an amount optimal for 10 Kg of body weight). The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

VI. Therapeutic Uses

Low doses of thionin (such as *Pyrularia* thionin) are effective for treatment of conditions or diseases that involve the immune system, for instance conditions (including clinical treatments) that inhibit (or suppress) the immune system. This effect can be enhanced by co-administering one or more additional immunostimulants (such as IL-2 or GM-CSF) with the thionin. General information about the therapeutic use of immunomodulatory compounds is well known, and can be found for instance in U.S. Pat. Nos. 5,632,983; 5,726,156; and 5,861,483.

A. Susceptible Diseases/Conditions

Immune deficiencies (e.g., deficiencies of one or more type of immune cells, or of one or more immunological factors) associated with immune deficiency diseases, immune suppressive medical treatment, acute and/or chronic infection, and aging can be treated using the methods and compositions described herein. A general overview of immunosuppressive conditions and diseases can be found in Harrisons "Principles of Internal Medicine," $14^{th}$ Edition, McGraw-Hill, 1998, and particularly in chapter 86 (Principles of Cancer Therapy), chapter 88 (Melanoma and other Skin Cancers), chapter 307 Primary Immune Deficiency Diseases), and chapter 308 (Human Immunodeficiency Virus Diseases).

Immune Suppressive Medical Treatment:

Many medical treatments can impair the immune system. Corticosteroids, for example, can reduce cell-mediated immunity. The predominant toxicity associated with cancer therapies (e.g., chemotherapy and radiotherapy) is destruction of proliferating cells, such as hematopoietic cells, responsible for maintenance of the immune and blood systems. Likewise, immune suppression and depletion of the immune system is required for bone marrow transplantation, in which immune cells are eliminated and subsequently replaced with transplanted cells. Certain known immunostimulants (e.g., erythropoietin and colony stimulating factors such as G-CSF, which is sometimes marketed under the name "NEUPOGEN™," U.S. Pat. No. 5,536,495) have been used previously to treat certain of these conditions by stimulating regeneration of the immune cells. The immunostimulatory compounds and mixtures of the invention can be used to stimulate the immune systems of patients suffering from medical treatment or iatrogenically induced immune suppression, including those who have undergone bone marrow transplants, chemotherapy, and/or radiotherapy.

Acute and/or Chronic Infection.

The ability of thionins to facilitate splenic T cell generation indicates that thionins could be used as a general immunostimulant to activate the immune system against various diseases, both chronic and acute. Subject infections include bacterial and viral infections, as well as infestations caused by eukaryotic pathogens and parasites.

More particularly, immunostimulatory thionin treatment can be used in the treatment of HIV disease. The ability of thionin protein to stimulate macrophages and cytotoxic T cells will be beneficial in helping to destroy HIV infected cells. In addition, the affinity of thionin protein for certain lipids in cell membranes (such as the affinity of PT to phosphatidyl serine) may inhibit fusion of the viral membrane with the cell membrane.

Aging-Linked Immune Deficiency.

Activation of the immune system (via stimulation of T cell production) by thionin treatment (with or without an added immunostimulant) is also believed to be beneficial in aging subjects, in whom immune function is often compromised.

General Other Conditions.

In addition to immunosuppression caused by medical treatment and infection, the disclosed methods and compositions can be used to treat genetic and biochemical immune deficiencies.

Other conditions are known in which the immune system is compromised or suppressed. Any of these conditions would also benefit from the methods disclosed herein, or application of the described compositions. In general, the need for treatment with one of the methods or compositions of this invention can be determined by examining the immune status of a test subject, and comparing this immune status to a control or average immune state (a hypothetical "normal" subject). For example, bone marrow biopsies or peripheral blood lymphocytes can be sampled to assess immune function. Indications of reduced immune function include leukopenia, for example neutrophenia or lymphopenia, or evidence of diminished white blood cell function. Where the test subject has a reduced immune condition, such as a reduction in a peripheral white blood cell count to below normal, for example 25% below normal, the immunostimulatory methods and/or compositions of the invention should be considered as treatments to improve the immune suppressed condition.

B. Mode of Treatment

The compounds and peptides (or mixtures thereof) of this invention may be administered to humans, or other animals on whose cells they are effective, in various manners such as topically, orally, intravenously, intramuscularly, intraperitoneally, intranasally, intradermally, intrathecally, and subcutaneously. The particular mode of administration and the dosage regimen will be selected by the attending clinician, taking into account the particulars of the case (e.g. the subject, the disease, the disease state involved, and whether the treatment is prophylactic). Treatment may involve daily or multi-daily doses of compound(s) and/or peptide(s) over a period of a few days to months, or even years.

A therapeutically effective amount of a thionin (e.g., *Pyrularia* thionin), or combination of a thionin and IL-2, can be the amount of thioinin (and IL-2) necessary to stimulate the immune system of a subject (also referred to as an immunostimulatory effective amount of a thionin). Specific immunostimulatory effects that can be caused by thionin (e.g., *Pyrularia* thionin), and by thionin in combination with IL-2, are described herein. In some embodiments, an immunostimulatory amount of a thionin is an amount sufficient to stimulate an immune response (for instance, any of the stimulatory responses discussed herein) without causing a substantial cytotoxic effect (e.g., without killing more than 10% of cells in a sample).

An effective amount of thionin (or thionin/IL-2) may be administered in a single dose, or in several doses, for example daily, during a course of treatment. However, the effective amount of active protein(s) will be dependent on the specific thionin and/or interleukin protein(s) applied, the subject being treated, the severity and type of the affliction, and the manner of administration of the therapeutic protein(s). For example, a therapeutically effective amount of *Pyrularia* thionin can vary from about 0.05 mg/Kg body weight to about 0.5 mg/Kg body weight, while a therapeutically effective amount of IL-2 used in conjunction with a thionin can vary from about 1,000 units /Kg body weight to about 25,000 units /Kg body weight. More characteristically, interleukins are measured in terms of units, with one unit being the amount that will induce half-maximal incorporation of tritiated thymidine into interleukin-dependent cytolytic T cell lymphocytes. Thus, IL-2 units are keyed to the amount of IL-2 that will induce half-maximal incorporation of tritiated thymidine into IL-2-dependent cytolytic T cell lymphomas. By way of example, certain preparations of IL-2 used for the studies described herein were purchased from Sigma Chemical Co., St Louis, Mo., and 1 unit was equal to 0.18 ng/ml.

Site-specific administration of the disclosed compounds may be used, for instance by applying a thionin preparation to a precancerous region, a region of tissue from which a neoplasm has been removed, or a region suspected of being prone to neoplastic development.

If treatment is through the direct administration to the subject of cells expressing a thioinin (or related peptide) or thionin genetic fusion to another protein, such cells (e.g., transgenic pluripotent or hematopoietic stem cells or B cells), for example, may be administered at a dose of between about $10^6$ and $10^{10}$ cells, on one or several occasions. The number of cells will depend on the patient, as well as the binding peptide and cells chosen to express the protein.

A general strategy for transferring genes into donor cells is disclosed in U.S. Pat. No. 5,529,774, which is incorporated by reference. Generally, a gene encoding a protein or peptide having therapeutically desired effects is cloned into a viral expression vector, and that vector is then introduced into the target organism. The virus infects the cells, and produces the protein sequence in vivo, where it has its desired therapeutic effect. See, for example, Zabner et al., *Cell* 75:207-216, 1993. As an alternative to adding the sequences encoding a polo-box (or related peptide), binding peptide or a homologous protein to the DNA of a virus, it is also possible to introduce such a gene into the somatic DNA of infected or uninfected cells, by methods that are well known (Sambrook et al., In *Molecular Cloning: A Laboratory Manual*, Cold Spring Harbor, N.Y., 1989). These methods can be used to introduce nucleic acids encoding the herein-disclosed peptides into human cells to provide long-term inhibition of cellular proliferation. For example, gene therapy can be used to secrete the peptides in cells localized at or near a neoplasm, at or near a stem cell site, etc.

C. Combinations

The present invention also includes combinations of a thionin with one or more other agents useful in the treatment of an immune-related disorder, condition, or disease, e.g., immune suppression caused by a disease or a therapeutic treatment. For example, the compounds and/or peptides of this invention may be administered in combination with effective doses of other immunostimulants, anti-cancer agents, anti-inflammatories, anti-infectives, and/or vaccines. The term "administration in combination" or "co-administration" refers to both concurrent and sequential administration of the active agents.

Co-administration of PT with immunostimulants in vaccines is also useful in prevention and/or protection against diseases that affect the immune system.

Examples of immuno-modulators that can be used in combination with the compounds and/or peptides of the invention are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, and TNF (Genentech). As discussed herein, it has been found to be particularly beneficial to co-administer a thionin with an immunostimulatory compound such as an interleukin (e.g., IL-2) or a colony-stimulating factor (such as G-CSF). Co-administration of these compounds leads to a synergistic stimulation of the immune system, permitting either the same response with a smaller dose of agents, or a large response with the same dosage.

The combination therapies are of course not limited to the lists provided in these examples, but includes any composition for the treatment of an immune disorder, such as an immuno-suppressive disorder.

D. Timing of Treatment

Treatment of a subject using the immunostimulatory compositions of the invention may be indicated after (or while) the subject has received an anti-proliferative or other cytotoxic therapeutic treatment. Examples of anti-proliferatives compounds include the following: ifosamide, cisplatin, methotrexate, cytoxan, procarizine, etoposide, BCNU, vincristine, vinblastine, cyclophosphamide, gencitabine, 5-fluorouracie, paclitaxel, and doxorubicin.

In some embodiments of the invention, a subject is given a cytotoxic treatment, then monitored for a period of time (usually in the range of days to weeks) to determine if the treatment leads to an immunosuppressive effect. Such monitoring can include monitoring peripheral blood for leukopenia or pancytopenia, and/or monitoring T cell function. A subject that displays an immune suppression will be a candidate for treatment using the compounds (e.g., a thionin with or without an interleukin) and therapeutic methods of the disclosed invention.

VII. Kits

The thionins, thionin-derivatives, and thionin/interleukin combinations disclosed herein can be supplied in unit dosage forms or kits for use in stimulation of an immune system, or for the prevention and/or treatment of a disorder, condition or diseases (e.g., an immune-compromised condition). In such a kit, a clinically effective amount of one or more of the compounds or peptides (e.g., a thionin, with or without an interleukin) is provided in one or more containers. The compounds or peptides may be provided suspended in an aqueous solution or as a freeze-dried or lyophilized powder, for instance. In certain embodiments, the compounds or peptides will be provided in the form of a pharmaceutical composition.

Kits according to this invention can also include instructions, usually written instructions, to assist the user in treating a disorder, condition or disease (e.g., an immune-compromised) with a thionin, thionin-derivative, or thionin/interleukin combination. Such instructions can optionally be provided in non-printed format, such as in a computer readable medium.

The container(s) in which the compound(s) and/or proteins(s) are supplied can be any conventional container that is capable of holding the supplied form, for instance, microfuge tubes, ampoules, or bottles. In some applications, the therapeutic compound or peptide may be provided in pre-measured single use amounts in individual, typically disposable, tubes or equivalent containers.

The amount of an active compound or complex or combination supplied in the kit can be any appropriate amount, depending for instance on the market to which the product is directed. For instance, if the kit is adapted for research or clinical use, the amount of each thionin, thionin-derivative, or thionin/interleukin combination provided would likely be an amount sufficient for several treatments.

Certain kits according to this invention will also include one or more other agents useful in stimulating the immune system, or in inhibiting a tumor, e.g., in treating hyper-proliferation. For example, such kits may include one or more effective doses of other anti-proliferative or anti-cancer drugs, or an immunostimulant such as GM-CSF.

VIII. Thionin Gene Therapy

Gene therapy approaches for combating neoplasia, and tumors such as melanoma, in subjects are now made possible by the present invention.

Retroviruses have been considered a preferred vector for experiments in gene therapy, with a high efficiency of infection and stable integration and expression (Orkin et al., *Prog. Med. Genet.* 7:130-142, 1988). A full-length thionin gene or cDNA can be cloned into a retroviral vector and driven from either its endogenous promoter or from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

In order to express the thionin at a low level, sufficient to provide immunostimulation without toxicity, a relatively low-level promoter can be used in the gene therapy construct.

Recent developments in gene therapy techniques include the use of RNA-DNA hybrid oligonucleotides, as described by Cole-Strauss, et al. (*Science* 273:1386-1389, 1996). This technique may allow for site-specific integration of cloned sequences, thereby permitting accurately targeted gene replacement.

In certain embodiments, gene therapies vectors are preferentially targeted to proliferating (e.g., neoplastic) cells. Methods and viral strains that can be used for such proliferating cell-biased gene therapy are discussed in U.S. Pat. No. 6,045, 789, which is incorporated herein by reference in its entirety.

In addition to delivery of sequences encoding a thionin (either with or without an interleukin-encoding sequence) to cells using viral vectors, it is possible to use non-infectious methods of nucleic acid delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

The invention is illustrated by the following non-limiting Examples.

EXAMPLES

Example 1

Mitogen Assay

This example provides a straight forward assay for determining if a thionin or related agent has a mitogenic effect on white blood cells. This mitogenic effect is an indication that the agent stimulates immune function.

Murine spleen cells or human peripheral blood lymphocytes (PBLS) were obtained aseptically as described herein for use in the mitogen assay. When murine splenocytes were used, they were first treated with red cell lysing buffer (0.17 M Tris, 0.144 $NH_4C_1$, pH 7.2), washed in RPMI-10 (standard RPMI growth medium, Sigma Chemical Co., St. Louis, Mo., supplemented with 10% fetal bovine serum) and viable cells counted using Trypan Blue exclusion. Human PBLs were isolated from blood using HISTOPAQUE™-1077, a solution of FICOLL™ and sodium diatrizoate (Sigma Chemical Co., St. Louis, Mo.), and subsequent washings with RPMI-5 (RPMI supplemented with 5% fetal bovine serum) to remove platelets. Isolated lymphocytes were resuspended in RPMI-10 and a viable cell yield determined by Trypan Blue exclusion.

Drugs and known mitogenic controls were added in triplicate to a 96-well flat bottom microplate aseptically. The culture medium was RPMI-10. Splenocytes or human-lymphocytes were added at a concentration of $3-4\times10^5$ cells/well, to a final volume of 200 µl/well. The assay plate was incubated at 37° C. in a 5% $CO_2$ humidified incubator. At 48-50 hours, $^3$H-thymidine was added (1 µCi/well), and the plate was harvested approximately 16-18 hours later.

Mitogen assay microplates were harvested using an Inotech plate harvester (Inotech Biosystems International, Inc., Rockville, Md.). Counts per minute (cpm) per well were measured using the Berthold-Inotech Trace 96-plate reader (Inotech AT, Wohlen, Switzerland) and/or a scintillation counter (Packard Tri-carb 2100TR, Packard Instrument Co., Meriden, Conn.). Mitogenic activity was directly determined by comparing cpm levels to controls.

Example 2

Natural Killer Assay

This example provides an additional assay for determining if a thionin or related agent has a mitogenic effect on white blood cells. Activation of natural killer cells is an indication that the agent stimulates immune function.

Murine spleen cell and human peripheral blood lymphocytes (PBLs) were obtained as described in the procedure for the Mitogen Assay.

Drugs and control substances were added, using sterile techniques, to the wells of a 24-well plate, using RPMI-10 as the culture medium. Spleen cells or human lymphocytes were added last to the wells at a concentration of $4\times10^6$ cells per 2 ml total volume in the well. Splenocyte incubation was usually three days (65-70 hours) while human lymphocyte stimulation may be extended to four to five days. The cells were incubated at 37° C. in a humidified 5% $CO_2$ incubator.

On the day of harvest, $10^7$ target cells were labeled with 150 μCi of $^{51}$Cr (sodium chromate). Target cells used were YAC-I (murine Lymphoma) or K562 (human chronic myelogenous leukemia).

The cells were adjusted to $2\times10^7$ cells/ml in RPMI-10 and 150 μCi of $^{51}$Cr were added to 500 μl of the target cell suspension ($10^7$ total cells) and incubated in a 5% $CO_2$ humidified incubator for 1.5 hours. The labeled cells were washed three times with 10 ml RPMI-10 and then resuspended in 5 ml ($2\times10^6$ cells/ml). Supernatants from washings of labeled cells were isolated and contained under lead shielding.

The stimulated effector cells were thoroughly mixed and removed from individual wells of the 24-well plate and transferred to tubes for centrifugation at 200×g. The supernatants were decanted and the pelleted cells washed once with 2 ml RPMI-10. The cells were finally resuspended in a total volume of 500 μl at approximately $8\times10^6$ cells/ml in RPMI-10.

One hundred microliters of the effector cell suspension ($8\times10^5$ cells) were added in triplicate to a 96-well, V-bottom microplate. RPMI-10 was added to the wells designated for spontaneous release and total release of the target cells. One hundred microliters of the target cell suspension ($1\times10^4$ cells/well) were added to the wells for a total volume of 200 μl. The "total release" wells contained 15 μl of 9% Triton X-100, 85 μl of RPMI-10, and 100 μl of target cells.

The 96-well plate was centrifuged at 150×g for four minutes to gently bring the effector and target cells in contact. The plate was then incubated in a humidified 5% $CO_2$ incubator. After four hours, the assay plate was again centrifuged for five minutes at 250×g. One hundred microliters of the supernatant was carefully removed from each well and placed in 12 mm×75 mm glass tubes for counting in a gamma counter. The percent release was calculated using the following formula:

$$\% \text{ Release} = \frac{(\text{Experimental} - \text{Spontaneous})}{(\text{Total Release} - \text{Spontaneous})} \times 100.$$

Example 3

Non-Radioactive Natural Killer Assay

This example provides an alternative non-radioactive assay used for assessing natural killer cell activity, the Promega CYTOTOX 96™ non-radioactive assay (Promega, Madison, Wis.). This method involves a calorimetric alternative that quantitatively measures lactase dehydrogenase (LDH) released upon cell lysis, and thereby measures the activity of natural killer cells.

The $^{51}$Cr-release natural killer cell assay (as described above) was modified as follows:

1. RPMI-0 (RPMI with no added bovine fetal serum) was used to wash and resuspend effector cells and wash target cells.
2. RPMI-5 was used to plate target cells for the assay. Final concentration of FBS (fetal bovine serum) was 2.5% in the well. (Keeping the FBS concentration low is advantageous as FBS may contain low levels of LDH.)
3. Five wells were set up for each test instead of three wells. Two were effector cell spontaneous release control wells, without target cells and using RPMI-5 in the wells to equal a total amount of 200 μl.
4. There was also a lysis control and a culture medium background control.

The Promega CYTOTOX 96™ procedure (as provided in instructions from the manufacturer) was followed to measure the LDH release after a four-hour incubation period at 37° C. Fifty microliters of supernatant from each sample well were transferred to a 96-well flat bottom plate. Substrate solution (50 μl) was added and the plate is incubated for 30 minutes at room temperature, covered with foil. Fifty microliters of stop solution was then added. To ensure an accurate reading, all bubbles were removed before reading the absorbance of the enzymatic assay plate at 490 nm.

The calculated percent of LDH released was directly proportional to target cell death. The formula was as follows:

$$\% \text{ LDH Release} = \frac{[(\text{Experimental} - \text{Effector Spontaneous}) - (\text{Target Spontaneous})]}{(\text{Target Maximum} - \text{Target Spontaneous})} \times 100$$

Example 4

Preparation of Spleen Cells

This example provides a method by which spleen cells can be readily prepared for assaying the immunostimulatory effect of a thionin, or a thionin derivative, analog, mimetic, or fragment.

A selected mouse was euthanized in a $CO_2$ chamber (exposure time, about two minutes).

The mouse was secured on a dissecting tray, on its right side, and sprayed with 70% ethanol. The outer skin was peeled back and a small cut made in the peritoneal membrane above the spleen. The spleen was removed aseptically and placed in a sterile Petri dish containing 5 ml of RPMI-10.

The spleen was teased apart using two 20-gauge needles attached to 5 ml syringes. After the spleen was minced into very small particles, the blunt end of one syringe was used to gently mash large particles of tissue to release more cells. Using one syringe, the cell suspension was transferred to a sterile tube. Any debris was allowed to settle for a few minutes, and then the cell suspension was transferred to a 15-ml sterile conical centrifuge tube.

The cell suspension was centrifuged at 200×g for 10 minutes, the supernatant decanted, and the pelleted cells were treated with 3 ml of red cell lysing buffer (0.017M Tris, 0.144M $NH_4Cl$, pH 7.2) for five minutes at 37° C. The cell suspension was then centrifuged for 10 minutes, the supernatant decanted, and the cells resuspended in 10 ml of RPMI-10. Following one more centrifugation at 200×g, the cell pellet was resuspended in 5 ml RPMI-10 and a viable cell count is or was obtained by diluting 50 μl of the cell suspension 1 to 4 with 0.4% Trypan Blue. Viable cells were counted using a hemocytometer. Cells were stored at 4° C. and examined within two hours. There was little loss of viability within this time period.

Example 5

In Vivo Immunostimulatory Activities of PT

This example provides a description of the results from several experiments in which the immunostimulatory activities of the representative thionin, *Pyrularia* thionin were determined.

C57BL/6NCr female mice (20 g), approximately 50 days old, were shaved in the abdominal area, ear notched for identification, and, two or three days prior to receiving tumor cells, pre-injected subcutaneously with the immunostimulating drugs described.

On "day zero," B16F10 melanoma tumor cells, cultured in αMEM medium with 10% FBS, were injected intradermally ($10^5$ cells in 0.1 ml) in the center of the mouse abdomen using a 26 gauge ½ inch needle. Four to five hours later, the drug treatment (as specified) was injected intradermally in a different area of the abdomen than the site of the tumor injection.

Intradermal treatments using the immunostimulatory drug (as specified) continued either every other day or on a Monday-Wednesday-Friday injection schedule. Control tumors (in mice not receiving an immunostimulatory drug) usually formed within seven to ten days. Tumors were examined by visual inspection, measured (length by width), and the area of any resulting lesion was recorded as $mm^2$ every five days.

Mice were euthanized by $CO_2$ inhalation if the tumor exceeded 500 $mm^2$. Some experiments were terminated early if all mice in the control group were dead, but the experiments were not less than 20 days. The normal duration of an experiment was about 30 days.

In Vivo Inhibition of B16f10 Melanoma by Administration of PT

*Pyrularia* thionin, both alone and in combination with IL-2, was effective in preventing or retarding the development of melanoma tumors when C57BL/6NCr mice were pretreated before injection with B16F10 cells, which produce melanoma tumors. Injection of 3 μg of PT in a volume of 100 ml subcutaneously into C57 mice five days and two days prior to injection of B16 melanoma cells and three times weekly thereafter slowed the development of tumors compared to mice injected with saline. Co-administering 100 units of murine interleukin-2 (IL-2) with PT for the injections was even more effective, resulting in almost half of the mice failing to develop tumors. The results indicated that the treatment was activating either the macrophages or natural killer cells to lyse the injected tumor cells before they established a tumor.

The data demonstrating this anti-neoplastic effect are shown in Table 2. The most significant data relate to the experiments involving treatment with PT and IL-2. For these experiments, 11 of 24 treated mice failed to develop tumors. Experiments with CS53 fibrosarcoma tumor cells and C3H female mice showed a similar response with fewer tumors developing and lower tumor volumes in mice treated with PT and IL-2.

For two experiments employing 5 μg PT plus 100 units of IL-2 injected subcutaneously, not included in the data of Table 2, the protection against injected melanoma cells was modest. In another experiment with 4 mice, treated with only 1 μg PT and 100 units IL-2, no mice developed a visible tumor. Data from a similar experiment are shown in FIG. 2, which depicts the typical response reported in Table 2 for 3 μg of PT. For this experiment, four mice were in the test group injected with drugs, and five mice were in the control group injected with saline. Of the four mice injected with 1 μg PT and 100 units of IL-2, only one mouse developed a tumor. Generally the best response to PT injected along with IL-2 was observed for 3 μg PT, but positive results can be obtained with somewhat smaller and larger amounts. There is little protection above a dose of 5 μg PT per mouse (with IL-2), which likely indicates the cytotoxic effect of PT directly on the immune cells of the mouse is beginning to take effect.

Inhibition of Metastasis of Tumor Cells by Injection of PT/IL-2

The data from Table 2 and FIG. 2 indicate that PT alone, and in combination with IL-2, did not cause remission of established tumors, indicating that its effect was not a cytotoxic effect on the tumor cells in an established tumor. Rather, thionin or thionin/IL-2 acted indirectly to inhibit the injected tumor cells from developing into a tumor. This implicates the immune system in the killing of the injected tumor cells. This mechanism of action in inhibiting (including preventing) the injected tumor cells from developing into a tumor indicates that the treatment also can be used to prevent metastasis (spread of malignant cells to parts of the body other than the site of the primary tumor).

Evidence for inhibition of metastasis is further demonstrated in Table 3, which contains data obtained by injecting $5 \times 10^4$ B16 cells loaded with radioactive $^{51}Cr$ (as described above) intravenously into the tail vein of C57 mice. Movement of the radioactive $^{51}Cr$ into body organs was assayed by measuring the radioactivity in the organ 26 hours after injection of the labeled B16 cells. The mice were given two injections of PT (3 μg) and IL-2 (100 units) on days -5 and -2 (i.e., five and two days prior to injection of the B16 cells), to activate the immune system. $^{51}Cr$ loaded cells lysed by the action of the activated natural killer cells release $^{51}Cr$, which is largely excreted by the kidneys, resulting in reduced retention of radioactivity in organs of those mice whose natural killer cells were activated by the injection of PT and IL-2.

TABLE 2

PT and IL-2 inhibit development of B16 melanoma tumors in C57 mice.

| | Number of Experiments | Days of Experiments | Treatment | Mice per Experiment | Total Mice in Experiments | Mice w/o Tumors | Average Tumor Size $mm^2$ | Number of Deaths |
|---|---|---|---|---|---|---|---|---|
| I. | 3 | 25-31 | Control | 5-6 | 17 | 0 | 435 | 6 |
| | | | + IL-2 | 4 | 12 | 0 | 364 | 1 |
| II. | 4 | 20-31 | Control | 4-6 | 21 | 0 | 302 | 4 |
| | | | + PT | 3-4 | 15 | 1 | 191 | 1 |
| III. | 7 | 24-31 | Control | 4-6 | 30 | 0 | 268 | 4 |
| | | | + PT + IL-2 | 3-5 | 24 | 11 | 46 | 2 |

This table includes data for three types of experiments: control mice with 0.01 M phosphate buffered saline but no drug injection; mice injected with IL-2; mice injected with PT; and mice injected with both compounds. The number of experiments in each category is indicated. Experimental procedures are described above. Drugs were administered subcutaneously: 3 μg PT, 100 units IL-2.

TABLE 3

Inhibition of metastasis of tumor cells by injection of PT/IL-2

| Organ measured | Control Mice (CPM) | PT/IL-2 Mice (CPM) | Estimated percent of control |
|---|---|---|---|
| Lungs | 746 ± 69 | 63 ± 0.7 | 8.4 |
| Kidneys | 3,610 ± 467 | 570 ± 31 | 16 |
| Spleen | 1,354 ± 691 | 44 ± 0.4 | 3.2 |
| Blood | 542 ± 170 | 99 ± 2 | 18 |
| Total | 6,252 ± 1189 | 766 ± 33 | 12 |

B16 cells loaded with $^{51}Cr$ were injected in the tail vein of two mice treated with 3 μg of PT and 100 units of IL2, five and then again three days prior to injection of $5 \times 10^4$ B16 melanoma cells loaded with $^{51}Cr$. The numbers represent radioactivity (cpm) detected in the organs and the blood as listed, and are averages of two mice included in each experiment.

Injection of PT and IL-2 into C57 mice stimulates the immune system and inhibits the metastasis potential of B16 tumor cells into cellular organs. As shown in Table 3, mice that received pre-treatment with PT and IL-2 showed only 12% of the amount of retained radioactivity compared to control mice, on average over all tissues tested. Specific tissues, such as lungs and spleen, showed an even greater reduction in $^{51}Cr$ retention.

In another experiment designed to measure metastatic potential, $5 \times 10^4$ B16 melanoma cells were injected intravenously into the tail veins of C57 female mice. Six mice were used for a control group and six mice were injected subcutaneously with 3 μg PT and 100 units of IL-2 three days before injection of the B16 cells. This treatment activated the natural killer cells. At the end of weeks 2, 3, 4, 5, 7, and 8 one mouse in each group was sacrificed and examined microscopically for tumors developing in the lungs, spleen, and thymus. Microscopically, a total of four tumors were seen in the control group, one for each mouse sacrificed after weeks 2, 4, 5, and 8. For the treated group there was only one microscopic tumor on the mouse sacrificed on week 8. These data show a significantly slower development of metastatic tumors in the mice treated with PT and IL-2.

PT Stimulates Mitogen Activity in Splenocytes and hPBLs

To test whether PT stimulates mitogen activity, splenocytes were incubated for two days with IL-2 (50 units/ml) or KLH (20 μg/ml) in conjunction with PT in the concentrations shown. Data from the results of these experiments are shown in Table 4. Figures represent the radioactivity counts of tritiated thymidine taken up during a subsequent 20-hour incubation period of cells incubated with tritiated thymidine in RPMI.

TABLE 4

Stimulation of mitogenic activity of murine splenocytes (Balb C) and non-adherent human PBLs in the presence of PT.

| Experiment: | RPMI CPM | RPMI + IL-2 CPM | RPMI + KLH CPM |
|---|---|---|---|
| Balb C splenocytes | | | |
| PT = 0 | 154 ± 48 | 2,379 ± 87 | 3,301 ± 255 |
| PT = 0.003 μg/ml | 230 ± 6 | 2,656 ± 110 | 3,957 ± 134 |
| PT = 0.03 μg/ml | 269 ± 57 | 3,017 ± 107 | 4,162 ± 200 |
| PT = 0.1 μg/ml | 268 ± 74 | 2,910 ± 351 | 4,254 ± 140 |
| PT = 0.3 μg/ml | 142 ± 10 | 2,395 ± 103 | 3,985 ± 101 |
| PT = 1.0 μg/ml | 107 ± 25 | 951 ± 122 | 1,742 ± 154 |
| Human PBLs | | | |
| PT = 0 | 401 ± 8 | 1,900 ± 64 | |
| PT = 0.01 μg/ml | 724 ± 212 | 2,584 ± 527 | |

The concentrations of PT are shown in the table, and when present IL-2 was 50 units/ml and the KLH was 20 μg/ml. Splenocytes were incubated with these drugs for two days. The numbers are the radioactivity counts (CPM) of tritiated thymidine taken up during a subsequent 20 hour incubation period of cells plus tritiated thymidine in RPMI. The experiments were performed in triplicate, and SEMS are included.

PT increased the mitogenic activity of both murine splenocytes and human peripheral blood lymphocytes (hPBL). The mitogenic activities were further increased by the addition of IL-2, which stimulates T cells, and by the antigenic protein keyhole limpet hemocyanin (KLH). In all cases, the maximal activities were observed when PT was in the incubation mixture.

Stimulation of Natural Killer Cells

The response to PT and IL-2 injected subcutaneously into C57 mice followed by B16 melanoma tumor cells (see Table 3) indicates that the protective effect of PT and the combination of PT and IL-2 is due to either the activation of macrophages to become tumoricidal, or activation of the Natural Killer (NK) cells by the injected drugs. The killing of tumor cells by the NK cells does not require recognition of specific tumor antigens by cells of the immune system, but is instead thought to be related to some unique property of the tumor cell membrane which is recognized by the NK cells, leading to cell killing.

Addition of PT stimulates both murine splenocytes and human PBLs to kill tumor cells through lysis. This effect is enhanced in the presence of IL-2. Experimentally, the YAC-1 tumor cell line is routinely used as a target cell for murine NK cells, and the K562 cell line is used as the target for human PBLs. The human prostate cell line DU145 was also included in the test. The data set out in Table 5 show an activation of both murine and human NK cells by PT and IL-2. For these experiments, the drugs, PT and IL-2, were included in the cell suspension and incubated for 48 hours. After this period, the splenocyte suspension was mixed with the YAC-1 target cells that had been loaded with $^{51}Cr$ for four hours. The human PBLs were added to a K562 or DU-145 cell suspension that had been similarly loaded. After a 30-minute incubation, the radioactivity in the supernatant fluid was counted as a measure of lysis of the target cells, which reflects NK activity. When present, PT was 0.01 μg/ml or 0.05 μg/ml and IL-2 was 50 U/ml.

TABLE 5

Stimulation of Natural Killer Cell by PT and IL-2.

| Immune cells | Conditions | % Cytotoxicity |
|---|---|---|
| Murine splenocytes | | |
| Swiss Webster | no additions | 0 ± 0.9 |
| | PT (0.01 μg/ml) | 3.4 ± 0.9 |
| | IL-2 (50 units/ml) | 16.3 ± 1.1 |
| | PT, IL-2 | 27.4 ± 1.7 |

TABLE 5-continued

Stimulation of Natural Killer Cell by PT and IL-2.

| Immune cells | Conditions | % Cytotoxicity |
|---|---|---|
| Human PBLs | | |
| K562 Target Cells | no additions | 1.6 ± 4.5 |
| | PT (0.01 µg/ml) | 8.4 ± 0.1 |
| DU-145 Target Cells | no additions | 2.1 ± 1.4 |
| | PT (0.05 µg/ml) | 11.5 ± 1.1 |

When present, PT was 0.01 or 0.05 µg/ml and IL-2 was 50 U/ml.
Target Cells loaded with $^{51}$Cr were YAC-1 for the murine effector cells and K562 or DU-145 cells for human non-adherent PBL effector cells. The ratio of effector cells (spleen or human PBL) to target cells (YAC-1, K562, or DU-145) was generally 80, with little variation.

The data in Table 5 show activation of both murine and human NK cells by PT and IL-2, as expected from the antitumor effect observed for injected PT and IL-2.

Stimulation of GM-CSF Mitogenic Activity

PT by itself shows a definite and consistent stimulation of mitogenic activity and natural killer cell activity with murine splenocytes. The protection of C57 mice against the melanoma tumor is definite and consistent. The response of PT in both cases is enhanced by the addition of IL-2 to the system. This indicates that the co-administration of PT and another immunostimulant provide enhanced treatment of cancer and other diseases that may be controlled or influenced by the immune system. Such treatment could include direct treatment of the disease, or alternatively, the use of PT in vaccines with appropriate antigens and/or other immunomodulators.

The efficacy of PT in stimulating immune responses was also tested with co-administration of granulocyte-macrophage colony-stimulating factor (GM-CSF). As shown in Table 6, the addition of PT to GM-CSF gives enhanced immune stimulation in the standard mitogen assay with murine (BALB C) spleen cells. Again, the concentrations of PT necessary to produce this synergistic effect were those that show stimulation of the mitogen assay without addition of other immunostimulants, and that were active along with IL-2 in the in vitro studied reactions. Similar synergistic effects will be seen in in vivo antitumor experiments for the melanoma tumor.

TABLE 6

PT Stimulates Mitogenic Activity of GM-CSF

| | Additions to RPMI: | | |
|---|---|---|---|
| | none Cpm | GM-CSF (5 ng/ml) Cpm | GM-CSF (20 ng/ml) Cpm |
| None | 262 | 1,024 | 1,170 |
| 0.01 µg/ml PT | 287 | 1,767 | 1,254 |
| 0.1 µg/ml PT | 243 | 822 | 1,549 |

The mitogen activity of granulocyte-macrophage colony-stimulating-factor (GM-CSF) is increased in the presence of PT at concentrations of PT which are stimulatory to the immune system. The data presented are counts per minute in the standard mitogen assay described above.

The data presented herein indicate that low doses of thionins, for instance *Pyrularia* thionin, are effective agents for treating cancer and other diseases involving the immune system. Co-administration of one or more immunomodulatory cofactor (such as IL-2 and GM-CSF) along with the thionin, enhances the efficacy of such treatment.

Example 6

Preparation of a Thionin Conjugate (Pt-βMe)

This example illustrates that thionins conjugated with immunostimulatory agents such as β-mercaptoethanol, have enhanced tumorigenic activity.

PT (40 mg) was dissolved in 400 µl of 0.01 M sodium phosphate buffer (pH 8.0) that had been degassed with nitrogen gas. N-succinimidyl-3-(2-pyridyldithio)propionate (SPDP), sufficient to give a 2:1 molar ratio (SPDP:PT) (4.7 mg), was dissolved in 200 µl of ethanol. The two solutions were chilled in ice, combined, and allowed to react at 4° C. for two hours. The SPDP derivative of PT was dried in a Savant SPEED VAC™ Concentrator (Savant, Holbrook, N.Y.), then purified by HPLC. The main peak was again dried and weighed.

The PT/SPDP derivative was reacted with β-mercaptoethanol in a 20:1 molar ratio (β-ME:PT/SPDP) in 1 ml of 0.01 M sodium phosphate buffer (pH 8.0) at room temperature for 45 minutes, and then placed in ice.

Using 3500 MW cut-off dialysis tubing, the PT derivative was dialyzed against 1 mM sodium phosphate buffer (pH 8.0) at 4° C., then lyophilized.

The drug that has been conjugated to PT is beta-mercaptoethanol (βME). This compound stimulates both the mitogenic and cytotoxic activities of murine splenocytes when added in the range of about 1 to 50 µM to the mitogen and natural killer cell assays (see, e.g. Examples 1 and 2). Using the conjugation reagent SPDP (described in methods section) to react with the amino groups of lysine in PT, and then conjugating this derivative with βME, via a disulfide linkage, a derivative of PT containing 2 molecules of βME per PT has been prepared, and its activity compared to the activities of PT itself. Table 7 shows the data obtained with PT and the βME derivative in a mitogen assay (Example 1) with murine splenocytes. In all cases, the activity of the βME derivative was greater than that of the parent PT. It should be noted that at a concentration of 0.1 µg/ml the concentration of PT is 20 nM, and the corresponding concentration of βME in the PT-βME derivative is 40 nM. At this concentration, the stimulations of the mitogen reaction by PT, as expected, was modest. Better stimulation by the PT-βME derivative was observed. βME alone is not active, giving no stimulation at this concentration.

TABLE 7

Mitogen Activity of PT-βME
CPM of Thymidine incorporated in Mitogen Assay

| | RPMI | KLH (20 µg/ml) |
|---|---|---|
| PT Concentration | | |
| 0 | 154 ± 48 | 3,301 ± 255 |
| 0.003 µg/ml | 230 ± 6 | N/D |
| 0.01 µg/ml | N/D | 3,737 ± 134 |
| 0.03 µg/ml | 269 ± 57 | 4,162 ± 200 |
| 0.1 µg/ml | 268 ± 74 | 4,284 ± 140 |
| 0.3 µg/ml | 147 ± 10 | 3,980 ± 101 |
| 1.0 µg/ml | 107 ± 25 | 1,747 ± 154 |
| PT-βME Concentration | | |
| 0 | 154 ± 48 | 3,301 ± 255 |
| 0.003 µg/ml | 303 ± 31 | N/D |
| 0.01 µg/ml | N/D | 5,253 ± 174 |

TABLE 7-continued

Mitogen Activity of PT-βME
CPM of Thymidine incorporated in Mitogen Assay

|  | RPMI | KLH (20 µg/ml) |
|---|---|---|
| 0.03 µg/ml | 415 ± 118 | 5,280 ± 467 |
| 0.1 µg/ml | 526 ± 222 | 5,106 ± 278 |
| 0.3 µg/ml | 460 ± 162 | 4,130 ± 61 |
| 1.0 µg/ml | 213 ± 40 | 3,565 ± 56 |

Mitogen activity (cpm of tritiated thymidine) of Balb/C splenocytes in the presence of PT, compared to the βME-PT derivative of the same concentration. The PT derivative contains 2 molecules of βME per molecule of PT. RPMI stands for Roswell Park Memorial Institute growth medium, a standard growth medium for cultured cells.

A similar increase in PT activity when conjugated to βME was observed in a cytotoxic natural killer assay by measuring $^{51}Cr$ release from YAC-1 cells loaded with the radioactive element. Data for PT and PT-βME for the concentration range of 0.01, 0.03, and 0.1 µg/ml are shown in Table 8. The activity of the PT-βME was higher than that of PT, being six times higher at 0.03 µg/ml and three times higher at the other concentrations

TABLE 8

Comparison of PT and PT-βME Derivative for Natural Killer Activity.

| Concentrations of PT or PT-derivative | % Cell Lysis PT | % Cell Lysis PT-derivative |
|---|---|---|
| 0 | 0 ± 0.3 | 0 ± 0.3 |
| 0.01 µg/ml | −0.9 ± 0.5 | 2.8 ± 0.5 |
| 0.03 µg/ml | 2.1 ± 0.2 | 4.4 ± 0.1 |
| 0.1 µg/ml | 1.8 ± 0.4 | 7.8 ± 2.7 |

Natural killer cell activity of Balb/C splenocytes in the presence of PT, and the βME-derivative at the same concentration. The βME-derivative contains two molecules of βME per PT molecule. The target cells were $^{51}Cr$ loaded YAC-1 cells for the standard natural killer assay (see Example 2). The experiments were performed in triplicate; averages and standard deviation are shown.

Example 7

ELISA Assays—Including Murine IL-1β, IL-2, IL-12

This example provides an indirect assay for determining if a thionin or related agent has an immunostimulatory effect. Increased production of certain immunostimulatory interleukins is an indication that the agent stimulates immune function. In addition, this method provides a high-throughput assay for selecting immunostimulatory, thionin related compounds.

Identical plates are set up for an immunoassay and a mitogen assay. Mouse splenocytes and immuno-stimulating drugs are plated in duplicate wells (immunoassay) and triplicate wells (mitogen assay) in 96-well microplates as described above. The incubation at 37° C. in a humidified 5% $CO_2$ incubator may vary from three to five days. At the end of the activation/proliferation period, the two identical plates are harvested as an immunoassay for cytokines or harvested as a mitogen assay (to which $^3H$-thymidine has been added approximately 16-18 hours earlier).

Immunoassay kits used to detect IL-1β, IL-2, and IL-12 were the murine Quantikine M™ kits produced by R&D Systems (Minneapolis, Minn.). The general procedure is the same for all interleukin cytokines, and is described in the instructions provided by the manufacturer. All reagents are used at room temperature, and are prepared according to kit instructions.

The immunoassay plate is centrifuged at 200×g to pellet all cells. A 50 µl aliquot of Assay Diluent is first added to the center of each special enzyme-coated well supplied with the kit. Next, 50 µl of standard, control or test sample of supernatant from the immunoassay incubation plate is added to each well. This is incubated at room temperatures for two hours.

Liquid is aspirated from the wells, and the wells are washed five times with surfactant diluted 1:25 with distilled water. A 100 µL aliquot of Conjugate is added to each well and incubated two hours at room temperature. The wells are again aspirated and each well washed five times.

One hundred microliters of Substrate Solution are added to each well and incubated 30 minutes at room temperature. Stop Solution (100 µl) is then added to each well. The color change is light blue to yellow (activity). The plate is read for absorbence at 450 nm and at 540 nm for background readings.

To calculate the results, the duplicate readings for each pair of standard, control, and test samples are averaged and the average background optical density readings are subtracted. A standard curve is constructed for the cytokine by plotting the mean absorbence for each standard on the y-axis against the concentration on the x-axis and drawing a best-fit curve. Picograms of cytokine are determined from the standard curve. Mitogenic activity determined from the cpm of $^3H$-thymidine is compared to the concentrations of cytokine in the experimental samples in the corresponding immunoassay.

These results show that PT activated murine and human macrophages. One measure of macrophage activation is the production of the cytokine interleukin-1 (IL-1) and also interleukin-12 (IL-12). Incubation of $3 \times 10^5$ Balb C murine spleen cells with 0.05 µg/ml PT was performed for 48 hours. The supernatant fluid was assayed with commercial ELISA kits for IL-1 and IL-12. The data presented in Table 9 show that treatment of the murine splenocytes with PT stimulates the production of these two cytokines. The amounts of IL-2 were also determined, but the results were not conclusive for stimulation of production of this cytokine. Some experiments gave less IL-2 and some more. This is likely a reflection of the state of the immune system in the experimental mice. The addition of KLH, an effective antigen, increased both IL-1 and IL-12 production, and the addition of PT along with the KLH further increased the production of these cytokines.

TABLE 9

PT stimulation of cytokine production by Balb C murine splenocytes.

| Experiment | IL-1 (pg/ml) | IL-12 (pg/ml) |
|---|---|---|
| 1. Balb C Splenocytes | | |
| Control | 3.9 ± 0 | 1.5 ± 0 |
| with PT (0.05 µg/ml) | 6.0 ± 0.2 | 5.6 ± 0.3 |
| with KLH (10 µg/ml) | 12.4 ± 0 | 21 ± 1.6 |
| with PT and KLH | 27 ± 1.1 | 25.5 ± 0.5 |
| 2. Balb C Splenocytes | | |
| Control | N/D | 21 ± 1.3 |
| with PT (0.05 µg/ml) | N/D | 24 ± 0.3 |
| 3. Balb C Splenocytes | | |
| Control | 2 ± 0.07 | N/D |
| with PT (0.05 µg/ml) | 2.4 ± 0 | N/D |

TABLE 9-continued

PT stimulation of cytokine production by Balb C murine splenocytes.

| Experiment | IL-1 (pg/ml) | IL-12 (pg/ml) |
|---|---|---|
| 4. Balb C. Splenocytes | | |
| Control | 9 ± 0.25 | N/D |
| with PT (0.05 μg/ml) | 14 ± 0.9 | N/D |
| with KLH (20 mg/ml) | 9 ± 0.4 | N/D |
| with PT and KLH | 29 ± 2.2 | N/D |

IL-1 and IL-12 production was determined by the ELISA technique using specific monoclonal antibodies. Splenocytes were incubated with the indicated drugs for 48 hours. The experiments were performed in triplicate.

Example 8

FITC Thy-1.2 Staining Procedure

This example provides a further assay for examining mitogenic effects of a thionin or related agent. This mitogenic effect is an indication that the agent stimulates immune function.

Using sterile technique the spleen or thymus was removed from a mouse euthanized by $CO_2$ gas. The organ was teased apart to collect splenocytes or thymocytes, respectively. The cells were treated with red cell lysing buffer at 37° C. to remove the erthyrocytes, then washed several times in culture medium, RPMI-10. The cells were counted using Trypan Blue exclusion to determine viable cell yield (as described above) and resuspended in PBS/1% BSA/0.1% sodium azide buffer (pH 7.2) at $2 \times 10^7$ cells/ml.

To a microfuge tube, in ice, was added 100 μl of cell suspension ($2 \times 10^7$ cells/ml). Five microliters of FcγR Block (CD16/CD32 Block; Pharmingen, San Diego, Calif.), diluted to 50 μg/ml with PBS/BSA/Azide Buffer, is added. The tube was gently mixed and kept on ice for three minutes.

One hundred microliters of Thy 1.2 FITC stain (10 μg/ml) were added and the tube was gently vortexed. Cells were stained for 30 minutes at 4° C., followed by centrifugation in a microfuge centrifuge at 4500 rpm for three minutes. The cells were washed twice with 500 μl ice-cold PBS/BSA/Azide buffer, and resuspended each time by gentle vortexing.

One hundred microliters of 1% paraformaldehyde (in PBS) were added to the cell pellet, and the cells were thoroughly mixed, then incubated 20 minutes at 4° C. The cells were then washed once with 500 μl of 2.19% glycine and resuspended in 500 μl of sterile PBS.

Fifteen microliters of the stained cell suspension were placed as two non-overlapping spots on a 1-mm thick glass slide that had been cleaned with ethanol. The cell droplets were allowed to dry without spreading or using a cover slip. The slides were air-dried in a hood, covered with aluminum foil to exclude light (in order to prevent photobleaching). If the slide was pre-cleaned and dried correctly, the droplets will naturally dry to a diameter of about 10 mm. The slides should be read within one week.

Cells were evaluated using a Zeiss oil-immersion microscope (UV-lamp, filter #47; Carl Zeiss Inc., Thornwood, N.Y.). Non-stained cells appeared medium-brown in color on a dark background. Fully stained cells had a fluorescent green ring. Partially stained cells that have a partial ring were counted separately. The percentage of non-stained, partially stained, and completely stained cells was determined. At least 200 cells per slide were scored, but usually about 300-400 cells were counted.

Data set out in Table 4, and discussed above, indicate that PT stimulates mitogen activity with murine splenocytes in vitro. This could come about through the action of activated macrophages on T cells by IL-1 production and antigen presentation to the T cells. Table 10 shows the percentage of T cells in the spleen and thymus after injection of 5 or 10 μg of PT intraperitoneally into Swiss Webster mice of varying ages. T cells were detected with fluorescent-labeled (FITC) Thy 1.2 monoclonal antibody, which is a general antibody for all T cells. The cells were counted manually with a fluorescent microscope, and the data are divided into cells with no stain (no fluorescence), cells with partial staining (medium fluorescence), and cells with intense staining (high fluorescence). The mice were injected with the indicated amount of PT intraperitoneally and the animals sacrificed after three days to obtain the spleen and thymus.

TABLE 10

Injection of *Pyrularia* thionin stimulate development of murine T cells in Swiss Webster mice.

| Experiment | Treatment | Splenic cells | | | Thymus cells | | |
|---|---|---|---|---|---|---|---|
| | | No Fluor. | Medium Fluor. | High Fluor. | No. Fluor. | Medium Fluor. | High Fluor. |
| 1. 7 week male mice | none | 69 ± 4.2 | 13 ± 1.1 | 18 ± 2.8 | | | |
| | 10 μg PT | 46 ± 0.4 | 24 ± 4.2 | 30 ± 5.0 | | | |
| 2. 6 month male mice | none | 50 ± 3.3 | 21 ± 0.3 | 29 ± 3.5 | | | |
| | 10 μg PT | 32 ± 1.1 | 36 ± 2.1 | 32 ± 1.4 | | | |
| 3. 4 month females | none | 50 ± 2.2 | 24 ± 2.1 | 26 ± 1.5 | 48 ± 3.3 | 27 ± 1.4 | 25 ± 3.5 |
| | 5 μg PT | 41 ± 3.5 | 28 ± 2.2 | 31 ± 2.5 | 32 ± 4.4 | 29 ± 1.5 | 39 ± 2.9 |

Experiments were performed in triplicate, and SEM values are shown.

Example 9

Binding of PT to Mouse Spleen Cells

This example demonstrates that the thionin PT binds to the surface of spleen cells, and provides the relative affinities of two apparent binding sites.

Splenocytes are isolated from the spleens of selected mice (as described herein), treated to remove red cells, resuspended in PBS after washing, and counted using Trypan Blue exclusion. The average yield of spleen cells (splenocytes) from one spleen is $1-1.5 \times 10^8$ cells. A desired concentration of cells per sample tube in the binding assay is more than $5 \times 10^6$ cells/ml.

The protocol for the binding assay has been previously described (Vernon and Rogers, *Toxicon* 30:711-721, 1992). Reactions were carried out in a total volume of 400 µl in each microcentrifuge tube (160 µl PBS with $^{125}$I-labeled PT at varying concentrations with 240 µl of spleen cell suspensions).

A total of $10^7$ spleen cells were placed in each of the reaction microfuge tubes, and allowed to equilibrate at room temperature for five minutes. To each tube was added radiolabeled thionin (e.g., $^{125}$I-PT) in amounts from 0.1 to 20 µg/ml. The radiolabeled PT used in the experiments contained approximately $10^6$ counts/minute (0.3 µCi) per µg PT. The suspension was incubated at room temperature for 10 minutes, then placed on ice for an additional 10 minutes. The tubes were then centrifuged to pellet the cells.

The radioactivity in the supernatant fluid was determined from an aliquot removed from the tube. The plastic pipette tip used to transfer the aliquot was also put in the vial and counted in a gamma ray counter along with the transferred aliquot of the supernatant fluid, since this tip may absorb PT from the aliquot during transfer. The radioactivity amount determined represents the "free" PT, not bound to a cell.

After removal of the entire supernatant, the sedimented cells were washed twice in PBS, and the entire final washed suspension of cells was transferred to a vial for radioactivity counting. As with measurement of radioactivity in the supernatant, the pipette tip used to transfer the cell sample was added to the vial to include any PT that might be bound to the plastic tip. This measures the total "bound" PT.

Non-specific binding was determined in the presence of a 100-fold excess of non-radioactive iodinated PT. The binding data reported were obtained by subtracting the non-specific from the total binding. Triplicate assays were performed for each concentration of PT employed.

Stimulation of the immune reactions by PT observed in this study, in vitro mitogen and natural killer activities, takes place at concentrations between 0.003 and 0.05 µg of PT per ml. The amount used routinely is 0.01 µg/ml. The additional stimulation by IL-2 indicates an action of PT at these concentrations on cells of the immune system. This is in stark contrast to the concentrations of PT required to induce changes in the membrane structure of cells or phospholipid vesicles, extensively reported in the literature, which begin around 1 µg/ml and continue up to and above 20 µg/ml. Whereas lower concentrations stimulate the responses of immune cells, the higher concentrations are toxic to cells, as described above in the Introduction section. This distinction between low and high concentrations of PT is also seen in the in vivo antitumor experiments described in Table 2. The amount of PT injected subcutaneously to elicit the protective effect (with IL-2) was 3 µg. This dosage stimulates the immune system. To elicit the toxic effect of PT on mice in vivo, much higher concentrations are required. The $LD_{50}$ for a 20-gram mouse is 30 µg of PT, ten times greater than the concentration that shows the maximal protective (immunostimulatory) effect.

Figure 3:
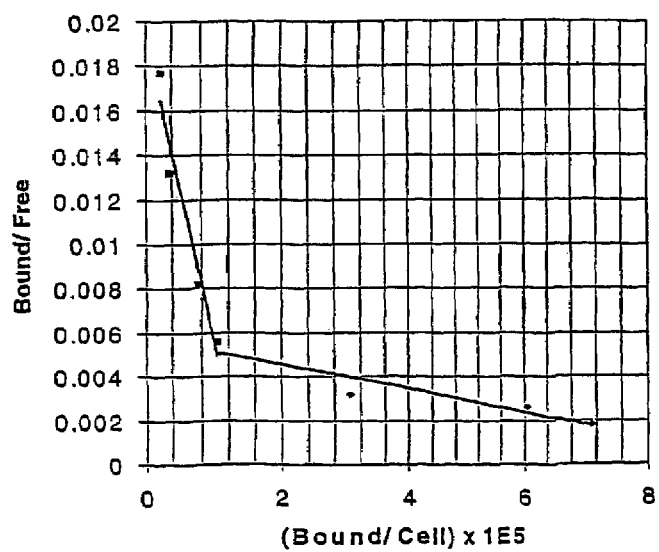

Evidence supporting two separate cellular responses to PT was obtained by measuring the extent of binding of PT to murine spleen cells. FIG. 3 shows data on the binding of radiolabeled PT (labeled with $^{125}$I) to isolated murine spleen cells. Two modes of binding are clearly seen. A high affinity binding site is shown for concentrations of PT up to 1 µg/ml, shown in the first four data points of the graph. The dissociation constant for binding to this high affinity site is 0.065 µM.

In addition, a low affinity binding site is shown for PT concentration up to 20 µg/ml, with a dissociation constant of 1.6 µM. This low affinity binding site observed with spleen cells and high PT concentrations relates to the data obtained previously for membrane-altering properties in this concentration range of PT and other thionins, as reported in the literature.

As expected the number of sites per cell for the high affinity site is lower, at $1.4 \times 10^5$, indicating binding to a membrane protein, and the number for the low affinity site is $1 \times 10^6$, reflecting the high number of binding sites with phospholipids in the cell membrane.

This invention provides immunostimulatory methods that employ low levels of thionin, either alone or in combination with interleukin-2. It will be apparent that the precise details of these methods and the described media may be varied or modified without departing from the spirit of the described invention. We claim all such modifications and variations that fall within the scope and spirit of the claims below.

---

I claim:

1. A method of stimulating immunity, comprising administering to a subject having a melanoma an immunostimulatory effective amount of *Pyrularia* thionin or *Pyrularia* thionin-compound conjugate; wherein the *Pyrularia* thionin or *Pyrularia* thionin-compound conjugate is administered in a dose that is immunostimulatory but substantially non-cytotoxic, and wherein stimulating immunity inhibits development or metastasis of the melanoma, and wherein stimulating immunity comprises activating macrophages, inducing mitosis in an immune cell in the subject, stimulating natural killer cell activity, stimulating the differentiation and proliferation of T cells in the subject, or a combination of two or more thereof.

2. The method of claim 1, comprising administering to the subject an immunostimulatory effective amount of *Pyrularia* thionin; wherein the *Pyrularia* thionin is administered in a dose that is immunostimulatory but substantially non-cytotoxic.

3. The method of claim 1, further comprising administering to the subject a therapeutically sufficient amount of a non-thionin immunostimulatory compound.

4. The method of claim 3, wherein the non-thionin immunostimulatory compound is a cytokine.

5. The method of claim 4, wherein the cytokine is an interleukin or a colony-stimulating-factor.

6. The method of claim 5, wherein the cytokine is IL-2.

7. The method of claim 1, wherein the *Pyrularia* thionin is administered in a dose of about 50 μg/Kg body weight to about 250 μg/Kg body weight.

8. The method of claim 1, wherein the *Pyrularia* thionin is administered in the form of a pharmaceutical composition comprising a pharmaceutically acceptable carrier.

9. The method of claim 1, wherein the stimulated natural killer cell activity is effective against tumor cells.

10. The method of claim 3, wherein the non-thionin immunostimulatory compound comprises GM-CSF, G-CSF, or saponin derivative QS-23.

11. The method of claim 1 wherein the *Pyrularia* thionin or *Pyrularia* thionin-compound conjugate is administered subcutaneously.

12. The method of claim 11 wherein the *Pyrularia* thionin or *Pyrularia* thionin-compound conjugate is administered in combination with IL-2.

13. The method of claim 1 wherein the *Pyrularia* thionin or *Pyrularia* thionin-compound conjugate is administered subcutaneously in combination with IL-2.

14. A method of stimulating immunity, comprising administering to a subject having a melanoma an immunostimulatory effective amount of *Pyrularia* thionin or *Pyrularia* thionin-compound conjugate and a therapeutically sufficient amount of IL-2; wherein the *Pyrularia* thionin or *Pyrularia* thionin-compound conjugate is administered in a dose that is immunostimulatory but substantially non-cytotoxic, and wherein stimulating immunity inhibits development of the melanoma or inhibits metastasis of the melanoma.

15. The method of claim 14, wherein stimulating immunity comprises activating macrophages, inducing mitosis in an immune cell in the subject, stimulating natural killer cell activity, stimulating the differentiation and proliferation of T cells in the subject, or a combination of two or more thereof.

16. The method of claim 14, wherein the *Pyrularia* thionin or *Pyrularia* thionin-compound conjugate is administered subcutaneously.

17. The method of claim 14, wherein the IL-2 is administered subcutaneously.

18. The method of claim 14, wherein the *Pyrularia* thionin is administered in a dose of about 50 μg/Kg body weight to about 250 μg/Kg body weight.

19. The method of claim 14, wherein the *Pyrularia* thionin or IL-2, or both, is administered in the form of a pharmaceutical composition comprising a pharmaceutically acceptable carrier.

* * * * *

UNITED STATES PATENT AND TRADEMARK OFFICE
CERTIFICATE OF CORRECTION

PATENT NO. : 7,572,436 B1 Page 1 of 1
APPLICATION NO. : 10/380237
DATED : August 11, 2009
INVENTOR(S) : Vernon It is certified that error appears in the above-identified patent and that said Letters Patent is hereby corrected as shown below:

Title Page Item [56]

Add: 5,637,563 A   6/1997  Khwaja

Column 14, line 4: "Therefor," should read --Therefore--

Column 25, line 49: "calorimetric" should read --colorimetric--

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,572,436 B1
APPLICATION NO. : 10/380237
DATED : August 11, 2009
INVENTOR(S) : Leo P. Vernon Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1622 days.

Signed and Sealed this

Seventh Day of September, 2010

David J. Kappos
*Director of the United States Patent and Trademark Office*

SEQUENCE LISTING

```
<160> NUMBER OF SEQ ID NOS: 11

<210> SEQ ID NO 1
<211> LENGTH: 47
<212> TYPE: PRT
<213> ORGANISM: Pyrularia thionin

<400> SEQUENCE: 1

Lys Ser Cys Cys Arg Asn Thr Trp Ala Arg Asn Cys Tyr Asn Val Cys
1               5                   10                  15

Arg Leu Pro Gly Thr Ile Ser Arg Glu Ile Cys Ala Lys Lys Cys Asp
            20                  25                  30

Cys Lys Ile Ile Ser Gly Thr Thr Cys Pro Ser Asp Tyr Pro Lys
        35                  40                  45

<210> SEQ ID NO 2
<211> LENGTH: 46
```

```
<212> TYPE: PRT
<213> ORGANISM: Viscotoxin A3

<400> SEQUENCE: 2

Lys Ser Cys Cys Pro Asn Thr Thr Gly Arg Asn Ile Tyr Asn Ala Cys
 1               5                  10                  15

Arg Leu Thr Gly Ala Pro Arg Pro Thr Cys Ala Lys Leu Ser Gly Cys
             20                  25                  30

Lys Ile Ile Ser Gly Ser Thr Cys Pro Ser Tyr Pro Asp Lys
             35                  40                  45

<210> SEQ ID NO 3
<211> LENGTH: 46
<212> TYPE: PRT
<213> ORGANISM: Viscotoxin B

<400> SEQUENCE: 3

Lys Ser Cys Cys Pro Asn Thr Thr Gly Arg Asn Ile Tyr Asn Thr Cys
 1               5                  10                  15

Arg Leu Gly Gly Gly Ser Arg Glu Arg Cys Ala Ser Leu Ser Gly Cys
             20                  25                  30

Lys Ile Ile Ser Ala Ser Thr Cys Pro Ser Tyr Pro Asp Lys
             35                  40                  45

<210> SEQ ID NO 4
<211> LENGTH: 46
<212> TYPE: PRT
<213> ORGANISM: Viscotoxin A2

<400> SEQUENCE: 4

Lys Ser Cys Cys Pro Asn Thr Thr Gly Arg Asn Ile Tyr Asn Thr Cys
 1               5                  10                  15

Arg Phe Gly Gly Gly Ser Arg Glu Val Cys Ala Ser Leu Ser Gly Cys
             20                  25                  30

Lys Ile Ile Ser Ala Ser Thr Cys Pro Ser Tyr Pro Asp Lys
             35                  40                  45

<210> SEQ ID NO 5
<211> LENGTH: 46
<212> TYPE: PRT
<213> ORGANISM: Phoradendron

<400> SEQUENCE: 5

Lys Ser Cys Cys Pro Asn Thr Thr Gly Arg Asn Ile Tyr Asn Thr Cys
 1               5                  10                  15

Arg Phe Gly Gly Gly Ser Arg Pro Val Cys Ala Lys Leu Ser Gly Cys
             20                  25                  30

Lys Ile Ile Ser Gly Thr Lys Cys Asp Ser Gly Trp Asn His
             35                  40                  45

<210> SEQ ID NO 6
<211> LENGTH: 46
<212> TYPE: PRT
<213> ORGANISM: Crambin

<400> SEQUENCE: 6

Thr Thr Cys Cys Pro Ser Ile Val Ala Arg Ser Asn Phe Asn Val Cys
 1               5                  10                  15

Arg Leu Pro Gly Thr Ser Glu Ala Ile Cys Ala Thr Tyr Thr Gly Cys
             20                  25                  30
```

-continued

Ile Ile Ile Pro Gly Ala Thr Cys Pro Gly Asp Tyr Ala Asn
        35                  40                  45

<210> SEQ ID NO 7
<211> LENGTH: 45
<212> TYPE: PRT
<213> ORGANISM: Wheat beta

<400> SEQUENCE: 7

Lys Ser Cys Cys Lys Ser Thr Leu Gly Arg Asn Cys Tyr Asn Leu Cys
1               5                   10                  15

Arg Ala Arg Gly Ala Gln Lys Leu Cys Ala Asn Val Cys Arg Cys Lys
            20                  25                  30

Leu Thr Ser Gly Leu Ser Cys Pro Lys Asp Phe Pro Lys
        35                  40                  45

<210> SEQ ID NO 8
<211> LENGTH: 45
<212> TYPE: PRT
<213> ORGANISM: Wheat alpha 1

<400> SEQUENCE: 8

Lys Ser Cys Cys Arg Ser Thr Leu Gly Arg Asn Cys Tyr Asn Leu Cys
1               5                   10                  15

Arg Ala Arg Gly Ala Gln Lys Leu Cys Ala Gly Val Cys Arg Cys Lys
            20                  25                  30

Ile Ser Ser Gly Leu Ser Cys Pro Lys Gly Phe Pro Lys
        35                  40                  45

<210> SEQ ID NO 9
<211> LENGTH: 45
<212> TYPE: PRT
<213> ORGANISM: Wheat alpha 2

<400> SEQUENCE: 9

Lys Ser Cys Cys Arg Thr Thr Leu Gly Arg Asn Cys Tyr Asn Leu Cys
1               5                   10                  15

Arg Ser Arg Gly Ala Gln Lys Leu Cys Ser Thr Val Cys Arg Cys Lys
            20                  25                  30

Leu Thr Ser Gly Leu Ser Cys Pro Lys Gly Phe Pro Lys
        35                  40                  45

<210> SEQ ID NO 10
<211> LENGTH: 45
<212> TYPE: PRT
<213> ORGANISM: Barley alpha

<400> SEQUENCE: 10

Lys Ser Cys Cys Arg Ser Thr Leu Gly Arg Asn Cys Tyr Asn Leu Cys
1               5                   10                  15

Arg Val Arg Gly Ala Gln Lys Leu Cys Ala Gly Val Cys Arg Cys Lys
            20                  25                  30

Leu Thr Ser Thr Gly Ser Cys Pro Lys Gly Phe Pro Lys
        35                  40                  45

<210> SEQ ID NO 11
<211> LENGTH: 45
<212> TYPE: PRT
<213> ORGANISM: Barley beta

<400> SEQUENCE: 11

-continued

```
Lys Ser Cys Cys Arg Ser Thr Leu Gly Arg Asn Cys Tyr Asn Leu Cys
1               5                   10                  15
Arg Val Arg Gly Ala Gln Lys Leu Cys Ala Asn Ala Cys Arg Cys Lys
            20                  25                  30
Leu Thr Ser Gly Leu Ser Cys Pro Lys Gly Phe Pro Lys
        35                  40                  45
```